United States Patent
Ota et al.

(10) Patent No.: US 10,071,001 B2
(45) Date of Patent: *Sep. 11, 2018

(54) ABSORBENT ARTICLE HAVING ABSORBENT BODY AND DIFFUSION LAYER

(71) Applicant: LIVEDO CORPORATION, Shikokuchuo-shi, Ehime (JP)

(72) Inventors: Yoshihisa Ota, Mima-gun (JP); Motoko Nishida, Mima-gun (JP)

(73) Assignee: LIVEDO CORPORATION, Shikokuchuo-shi, Ehime (JP)

( * ) Notice: Subject to any disclaimer, the term of this patent is extended or adjusted under 35 U.S.C. 154(b) by 600 days.

This patent is subject to a terminal disclaimer.

(21) Appl. No.: 14/435,579

(22) PCT Filed: Sep. 12, 2013

(86) PCT No.: PCT/JP2013/074667
§ 371 (c)(1),
(2) Date: Apr. 14, 2015

(87) PCT Pub. No.: WO2014/061378
PCT Pub. Date: Apr. 24, 2014

(65) Prior Publication Data
US 2015/0297424 A1    Oct. 22, 2015

(30) Foreign Application Priority Data
Oct. 15, 2012 (JP) .................. 2012-228233

(51) Int. Cl.
*A61F 13/15* (2006.01)
*A61F 13/20* (2006.01)
(Continued)

(52) U.S. Cl.
CPC ............ *A61F 13/534* (2013.01); *A61F 13/53* (2013.01); *A61F 13/53717* (2013.01);
(Continued)

(58) Field of Classification Search
CPC ....... A61F 13/5323; A61L 15/42; A61L 15/60
See application file for complete search history.

(56) References Cited

U.S. PATENT DOCUMENTS 5,613,962 A    3/1997   Kenmochi et al.
5,668,078 A    9/1997   Sumiya et al.
(Continued)

FOREIGN PATENT DOCUMENTS

CN    101396316 A    4/2009
EP    0705643 B1    12/1999
(Continued)

OTHER PUBLICATIONS

Office Action dated Oct. 17, 2016, issued in Taiwanese application No. 102133332.(6 pages).
(Continued)

*Primary Examiner* — Michele M Kidwell
(74) *Attorney, Agent, or Firm* — Westerman, Hattori, Daniels & Adrian, LLP

(57) ABSTRACT

An objective of the present invention is to provide an absorbent article having an excellent absorption speed of body fluid and excellent dryness after absorbing body fluid. The absorbent article of the present invention comprises: an absorbent body where a water absorbent resin powder meeting the following requirements (a) to (c) is disposed, (a) an absorption speed measured by a vortex method: 20 seconds to 50 seconds, (b) a liquid passing speed under load: 10 seconds or less, (c) a moisture absorption blocking ratio: 5% or less; and a diffusion layer composed of a synthetic fiber assembly substantially having no water absorption.

20 Claims, 3 Drawing Sheets

(51) Int. Cl.
  *A61F 13/534* (2006.01)
  *A61L 15/60* (2006.01)
  *A61F 13/537* (2006.01)
  *A61L 15/22* (2006.01)
  *A61F 13/53* (2006.01)

(52) U.S. Cl.
  CPC ...... *A61F 13/53756* (2013.01); *A61L 15/225* (2013.01); *A61L 15/60* (2013.01); *A61F 2013/530481* (2013.01); *A61F 2013/530532* (2013.01); *A61F 2013/530547* (2013.01); *A61F 2013/530708* (2013.01)

(56) References Cited

U.S. PATENT DOCUMENTS

| | | | | |
|---|---|---|---|---|
| 5,676,660 | A * | 10/1997 | Mukaida | A61F 13/53 604/367 |
| 9,492,583 | B2 * | 11/2016 | Ota | A61L 15/24 |
| 2004/0024104 | A1 | 2/2004 | Ota et al. | |
| 2005/0221980 | A1 | 10/2005 | Adachi et al. | |
| 2006/0282052 | A1 | 12/2006 | Saito et al. | |
| 2007/0141338 | A1 | 6/2007 | Ishizaki et al. | |
| 2009/0036855 | A1 | 2/2009 | Wada et al. | |
| 2014/0364824 | A1 * | 12/2014 | Ota | A61L 15/42 604/372 |
| 2015/0065980 | A1 * | 3/2015 | Ota | A61F 13/537 604/372 |

FOREIGN PATENT DOCUMENTS

| | | |
|---|---|---|
| EP | 1325777 B1 | 12/2010 |
| JP | 04-504285 A | 7/1992 |
| JP | 11-005904 A | 1/1999 |
| JP | 2001-187088 A | 7/2001 |
| JP | 2006-057075 A | 3/2006 |
| JP | 2007-190170 A | 8/2007 |
| JP | 2008-237430 A | 10/2008 |
| JP | 2008-284190 A | 11/2008 |
| JP | 2010-017536 A | 1/2010 |
| JP | 2010-059254 A | 3/2010 |
| JP | 2010-185029 A | 8/2010 |
| JP | 2010-234368 A | 10/2010 |
| JP | 2011-178969 A | 9/2011 |
| JP | 2012-031278 A | 2/2012 |
| WO | 90/12130 A2 | 10/1990 |
| WO | 2005/092955 A1 * | 10/2005 ................ C08J 3/12 |

OTHER PUBLICATIONS

Extended European Search Report dated Feb. 9, 2016, issued in counterpart European Patent Application No. 13847865.6. (7 pages).
International Search Report dated Nov. 19, 2013, issued in corresponding application No. PCT/JP2013/074667.
Third Party Observation dated Feb. 13, 2015, issued in corresponding application No. PCT/JP2013/074667.
Office Action dated Feb. 27, 2018, issued in counterpart Chinese application No. 201380053812.6 (w/ English translation; 18 pages).

* cited by examiner

ABSORBENT ARTICLE HAVING ABSORBENT BODY AND DIFFUSION LAYER

FIELD OF THE INVENTION

The present invention relates to an absorbent article such as incontinence pads, disposable diapers, and sanitary napkins; and the present invention particularly relates to a technology for improving absorption performance.

DESCRIPTION OF THE RELATED ART

Absorbent articles such as incontinence pads, disposable diapers, and sanitary napkins include an absorbent body for absorbing and retaining body fluid excreted from body such as urine and menstrual blood. The absorbent body generally includes a water absorbent resin powder, and body fluid is absorbed and retained in the water absorbent resin powder inside the absorbent body. Water absorbent articles with improved absorption performance of body fluid have been proposed.

For example, Patent literature 1 discloses an absorbent article comprising a liquid permeable surface sheet, a liquid impermeable back sheet and a water retaining absorbent body disposed between the two sheet, wherein a nonwoven fabric having a basis mass of 20 g/m² to 100 g/m², a no-load thickness of 1 mm to 10 mm and a compression recovery rate (b/a×100) of 60% or more, is disposed between the back sheet and the absorbent body, between the surface sheet and the absorbent body or inside the absorbent body, or disposed at multiple positions of these positions (refer to paragraph 0014 and FIG. 2 to FIG. 4 of Patent literature 1).

Patent literature 2 discloses an absorbent article comprising an absorbent body, a top sheet disposed to cover the front surface of the absorbent body and at least a part of which is formed from a liquid permeable material, and a back sheet disposed on the rear surface of the absorbent body and formed from a liquid impermeable material, wherein the absorbent body has an aperture part penetrating from the front surface to the rear surface of the absorbent body, the top sheet is disposed on the front surface of the absorbent body, and a diffusion sheet with higher liquid permeability than the absorbent body is disposed on the rear surface of the absorbent body to cover the region including the opening of the aperture part (refer to paragraphs 0061 to 0062 and FIG. 1 to FIG. 10 of Patent literature 2).

Patent literature 3 discloses an absorbent article comprising a diaper or incontinent pad having a major axis and a minor axis and a length in excess of a width which comprises a top sheet, a back sheet and an absorbent core comprising at least one absorbent layer, wherein said article further comprises a tow comprising a synthetic fiber which is capable of spontaneously transporting water on the surface thereof and satisfies the following equation (refer to claim 11, and line 23 at upper right column of page 7 to line 10 at lower right column of page 7 of Patent literature 3).

$$(1 - X \cos \theta_a) < 0$$

[in the equation, $\theta_a$ is an advancing contact angle of water measured on a flat film made from the same material as the fiber and having the same surface treatment, if any, X is a shape factor of the fiber cross section that satisfies the following equation:

$$X = P_w / \{4r + (\pi - 2)D\}$$

(in the equation, $P_w$ is a wetted perimeter of the fiber, r is a radius of the circumscribed circle circumscribing the fiber cross section, and D is a minor axis dimension across the fiber cross section).]

CITATION LIST

Patent Literature

Patent literature 1: Japanese Patent Publication No. 2001-187088 A
Patent literature 2: Japanese Patent Publication No. 2008-284190 A
Patent literature 3: Japanese Patent Publication No. H04-504285 T

SUMMARY OF THE INVENTION

Examples of the method for improving absorption performance of the absorbent article include: a method of increasing the amount (filling ratio) of the water absorbent resin powder; and a method of making as many water absorbent resin particles as possible contribute to the body fluid absorption by disposing a body fluid diffusing member. However, when a nonwoven fabric was used as the body fluid diffusing member as described in the cited literatures 1 and 2, fibers of the nonwoven fabric are adhered each other or tangled together in a high density, thus the liquid passing property becomes poor. As a result, the absorption speed improvement effect of the absorbent article is small. In addition, when a fiber having a very high wettability with body fluid was used as the body fluid diffusing member as described in the cited literature 3, the body fluid is likely to remain on the fiber surface. As a result, dryness after absorbing body fluid tends to decrease.

On the other hand, in the case of increasing the amount of the water absorbent resin powder, when the body fluid is absorbed, the swollen water absorbent resin powders on the skin-contacting side are likely to come into contact with each other. As a result, a void as a passage for body fluid is closed, and the absorbent body cannot exhibit a required water absorbing ability. This phenomenon is called gel blocking. If gel blocking occurs, both the absorption speed and dryness after absorbing body fluid decrease.

The present invention has been made in view of the above circumstances, and an object of the present invention is to provide an absorbent article having an excellent absorption speed of body fluid and excellent dryness after absorbing body fluid.

The absorbent article of the present invention, which can solve the above problems, comprises:

an absorbent body where a water absorbent resin powder meeting the following requirements (a) to (c) is disposed, (a) an absorption speed measured by a vortex method: 20 seconds to 50 seconds, (b) a liquid passing speed under load: 10 seconds or less, (c) a moisture absorption blocking ratio: 5% or less; and a diffusion layer composed of a synthetic fiber assembly substantially having no water absorption.

In the present invention, the water absorbent resin powder used for the absorbent body has a high absorption speed of body fluid, and can readily pass the body fluid that is not absorbed immediately to a lower portion. Further, the diffusion layer composed of the synthetic fiber assembly can readily diffuse the body fluid in a planar direction and a thickness direction. Since the body fluid taken into the absorbent article is diffused in and absorbed by the nearly whole absorbent body, the absorbent article of the present invention has a high absorption speed. In addition, since the synthetic fiber assembly substantially has no water absorption, the body fluid is absorbed by the water absorbent resin powder finally. As a result, return of the excreted body fluid is unlikely to occur, thus surface dry feeling of the absorbent article is excellent.

A material of a synthetic fiber constituting the synthetic fiber assembly preferably has a solubility parameter ranging from 6.0 $(J/cm)^{1/2}$ to 14.5 $(J/cm^3)^{1/2}$. The water absorbent resin powder preferably has a bulk density ranging from 0.45 g/ml to 0.70 g/ml, an absorption ratio ranging from 40 g/g to 55 g/g, and a water retaining capacity ranging from 20 g/g to 45 g/g.

The water absorbent resin powder is preferably obtained by treating, with a surface modifier (B), a crosslinked polymer (A) obtained by polymerizing a monomer composition containing: a water-soluble ethylenically unsaturated monomer (a1) and/or a hydrolyzable monomer (a2) producing the water-soluble ethylenically unsaturated monomer (a1) by hydrolysis; and an internal crosslinking agent (b). An amount of the surface modifier (B) for the treatment preferably ranges from 0.001 part by mass to 1 part by mass with respect to 100 parts by mass of the crosslinked polymer (A). The surface modifier (B) is preferably at least one member selected from the group consisting of an amino-modified polysiloxane, a carboxy-modified polysiloxane, and silica.

The absorbent article is preferably an embodiment wherein the absorbent body comprises an air-laid water absorption layer obtained by an air laying method; and a mass ratio of the water absorbent resin powder to a total mass of the air-laid water absorption layer ranges from 62.0 mass % to 99.5 mass %. The absorbent article is also preferably an embodiment wherein the absorbent body comprises a liquid permeable first sheet, a second sheet, and the water absorbent resin powder disposed between the first sheet and the second sheet; and a mass ratio of the water absorbent resin powder to a total mass of the absorbent body is 60 mass % or more.

As the configuration of the absorbent article, a configuration wherein the absorbent body is disposed on the upper surface side of the diffusion layer is preferable. A planar view shape of the absorbent body is preferably substantially identical to a planar view shape of the diffusion layer.

The present invention can provide an absorbent article having an excellent absorption speed of body fluid and excellent dryness after absorbing body fluid.

DESCRIPTION OF THE PREFERRED EMBODIMENT

Figure 1:
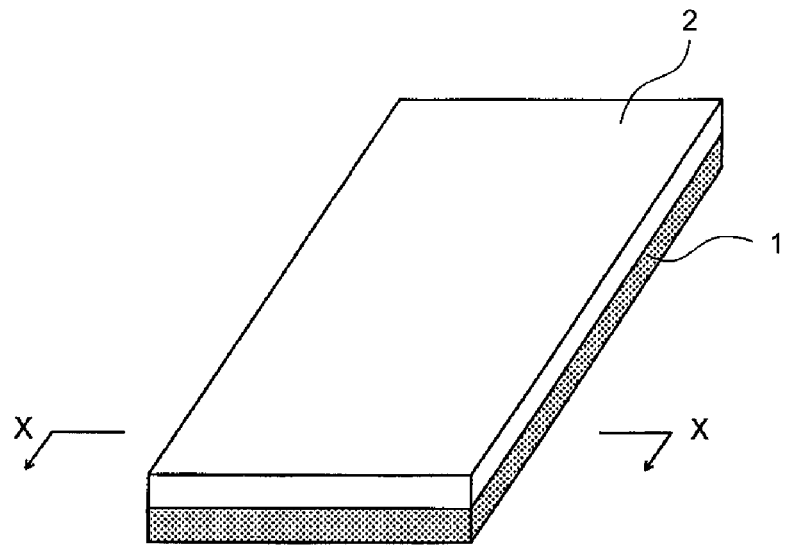
FIG. 1 is a schematic perspective view of an absorbent body and a diffusion layer according to a preferable embodiment 1 of the present invention.

The absorbent article of the present invention comprises:
an absorbent body where a water absorbent resin powder meeting the following requirements (a) to (c) is disposed.
(a) an absorption speed measured by a vortex method: 20 seconds to 50 seconds,
(b) a liquid passing speed under load: 10 seconds or less,
(c) a moisture absorption blocking ratio: 5% or less; and
a diffusion layer composed of a synthetic fiber assembly substantially having no water absorption.

In the present invention, the water absorbent resin powder used for the absorbent body has a high absorption speed of body fluid, and can readily pass the body fluid that is not absorbed immediately to a lower portion. Further, the diffusion layer composed of the synthetic fiber assembly can readily diffuse the body fluid in a planar direction and a thickness direction, and substantially has no water absorption, thus the body fluid is finally absorbed by the water absorbent resin powder. As a result, the absorbent article of the present invention has a high absorption speed of body fluid even in the case that large quantity of body fluid is taken into the absorbent article, and has excellent surface dry feeling since return of the excreted body fluid is unlikely to occur.

Absorbent Body

The water absorbent resin powder is disposed in the absorbent body for absorbing body fluid. The water absorbent resin powder used in the present invention will be described below. The water absorbent resin powder has (a) an absorption speed measured by a vortex method ranging from 20 seconds to 50 seconds. The absorption speed of the water absorbent resin powder measured by the vortex method is preferably 22 seconds or more, more preferably 25 seconds or more, and is preferably 48 seconds or less, more preferably 45 seconds or less. If the absorption speed exceeds 50 seconds, the body fluid cannot be sufficiently absorbed when large quantity of body fluid is excreted at a high speed at one time. As a result, liquid leakage may occur. The absorption speed is more preferred if it is lower, but if the absorption speed is less than 20 seconds, the stability of the water absorbent resin powder to urine, in particular, its stability to urine under load, may be lowered. The absorption speed measured by the vortex method is evaluated by measuring a time (seconds) taken to absorb body fluid. Thus, the shorter measured time (seconds) means the higher absorption speed.

The water absorbent resin powder has (b) a liquid passing speed under load of 10 seconds or less. The liquid passing speed under load is preferably 8 seconds or less, and more preferably 5 seconds or less. If the liquid passing speed under load exceeds 10 seconds, failure of diffusing body fluid is likely to occur within the absorbent body. Thus, liquid leakage may be likely to occur. The liquid passing speed under load is evaluated by measuring a time (seconds) taken for a certain amount of liquid to pass through a water absorbent resin powder that is made to absorb water to swell beforehand, in a state where a load is applied to the water absorbent resin powder. Thus, the shorter measured time (seconds) means the higher absorption speed.

The water absorbent resin powder has (c) a moisture absorption blocking ratio of 5% or less. The moisture absorption blocking ratio is more preferably 4% or less, and even more preferably 3% or less. If the moisture absorption blocking ratio exceeds 5%, the water absorbent resin powder is likely to aggregate. Thus, when an absorbent body is manufactured, problems arise such as the water absorbent resin powder being easily stuck in a feed pipe in a manufacturing machine or a manufacturing line, or the water absorbent resin powder not being able to be uniformly applied to a nonwoven fabric. In addition, return of excreted body fluid may occur.

The water absorbent resin powder preferably has a bulk density in a range from 0.45 g/ml to 0.70 g/ml. The bulk density of the water absorbent resin powder is more preferably 0.50 g/ml or more, and even more preferably 0.52 g/ml or more, and is more preferably 0.68 g/ml or less, and even more preferably 0.65 g/ml or less. The bulk density is an index of the shape of the water absorbent resin powder. If the bulk density falls within the above range, a void is easily formed for a passage of body fluid between the water absorbent resin powders. As a result, the absorption speed and repeated-absorption speed become favorable. The method for measuring the bulk density will be described later.

The water absorbent resin powder preferably has an absorption ratio of 40 g/g or more, more preferably 42 g/g or more, and even more preferably 44 g/g or more, and preferably has an absorption ratio of 55 g/g or less, more preferably 53 g/g or less, and even more preferably 51 g/g or less. The absorption ratio is a measure indicating how much water the water absorbent resin powder can absorb. If the absorption ratio is less than 40 g/g, a large amount of the water absorbent resin powder has to be used in order to maintain an absorption capacity at a predetermined level, and thus it is difficult to manufacture a thin absorbent body. In light of prevention of liquid leakage, the absorption ratio is more preferred if it is greater, but the absorption ratio is more preferably 55 g/g or less. This is because if the absorption ratio exceeds 55 g/g, the stability of the water absorbent resin powder to urine tends to decrease.

The water absorbent resin powder preferably has a water retaining capacity of 20 g/g or more, more preferably 22 g/g or more, and even more preferably 24 g/g or more, and preferably has a water retaining capacity of 45 gig or less, more preferably 43 g/g or less, and even more preferably 40 g/g or less. The water retaining capacity is a measure indicating how much absorbed liquid the water absorbent resin powder can retain. If the water retaining capacity is less than 20 g/g, a large amount of the water absorbent resin powder has to be used in order to maintain a body fluid-retaining capacity at a predetermined level, and thus it may be difficult to manufacture a thin absorbent body. In light of prevention of liquid leakage, the water retaining capacity is more preferred if it is greater, but the water retaining capacity is more preferably 45 g/g or less. This is because if the water retaining capacity exceeds 45 g/g, the stability of the water absorbent resin powder to urine tends to decrease.

The absorption speed measured by the vortex method, the liquid passing speed under load, the moisture absorption blocking ratio, the bulk density, the absorption ratio, and the water retaining capacity of the water absorbent resin powder can be adjusted by, for example, appropriately selecting a composition of a crosslinked polymer, a type of a surface modifier, a particle size of the water absorbent resin powder, a drying condition, and the like.

The water absorbent resin powder is preferably obtained by treating the surface of a crosslinked polymer (A) with a surface modifier (B). The crosslinked polymer (A) is preferably obtained by polymerizing a monomer composition containing a water-soluble ethylenically unsaturated monomer (a1) and/or a hydrolyzable monomer (a2) producing the water-soluble ethylenically unsaturated monomer (a1) by hydrolysis; and an internal crosslinking agent (b) as essential components.

First, the crosslinked polymer (A) will be described. The water-soluble ethylenically unsaturated monomer (a1) is not particularly limited, but a monomer having at least one water-soluble substituent and an ethylenically unsaturated group, or the like can be used. The water-soluble monomer means a monomer having a property of being dissolved at least in an amount of 100 g in 100 g of water at 25 degrees centigrade. In addition, the hydrolyzable monomer (a2) is hydrolyzed with water at 50 degrees centigrade, by the action of a catalyst (an acid, a base, or the like) where necessary, to produce the water-soluble ethylenically unsaturated monomer (a1). The hydrolysis of the hydrolyzable monomer (a2) may be conducted during or after the polymerization of the crosslinked polymer (A) or both during and after the polymerization of the crosslinked polymer (A). However, the hydrolysis of the hydrolyzable monomer (a2) is preferably conducted after the polymerization of the crosslinked polymer (A) in light of the molecular weight of the obtained water absorbent resin powder and the like.

Examples of the water-soluble substituent include a carboxyl group, a sulfo group, a sulfoxy group, a phosphono group, a hydroxyl group, a carbamoyl group, an amino group, or salts thereof and an ammonium salt. A salt of a carboxyl group (a carboxylate), a salt of a sulfo group (a sulfonate), and an ammonium salt are preferred. In addition, examples of the salts include salts of alkali metal such as lithium, sodium, and potassium and salts of alkaline earth metal such as magnesium and calcium. The ammonium salt may be any of salts of primary to tertiary amines or a quaternary ammonium salt. Among these salts, in light of absorption properties, alkali metal salts and ammonium salts are preferred, and alkali metal salts are more preferred, and sodium salts are further preferred.

As the water-soluble ethylenically unsaturated monomer having a carboxyl group and/or a salt thereof, an unsaturated carboxylic acid having 3 to 30 carbon atoms and/or a salt thereof are preferred. Specific examples of the water-soluble ethylenically unsaturated monomer having a carboxyl group and/or a salt thereof include unsaturated monocarboxylic acids and/or salts thereof such as (meth) acrylic acid, (meth) acrylic acid salt, crotonic acid, and cinnamic acid; unsaturated dicarboxylic acids and/or salts thereof such as maleic acid, maleate, fumaric acid, citraconic acid, and itaconic acid; and monoalkyl (1 to 8 carbon atoms) esters of unsaturated dicarboxylic acids and/or salts thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that in the description of the present invention, "(meth) acrylic" means "acrylic" and/or "methacrylic".

As a water-soluble ethylenically unsaturated monomer having a sulfo group and/or a salt thereof, a sulfonic acid having 2 to 30 carbon atoms and/or a slat thereof are preferred. Specific examples of the water-soluble ethylenically unsaturated monomer having a sulfo group and/or a salt thereof include aliphatic or aromatic vinyl sulfonic acids such as vinyl sulfonic acid, (meth) allyl sulfonic acid, styrene sulfonic acid, and alpha-methyl styrene sulfonic acid; (meth) acryloyl-containing alkyl sulfonic acids such as (meth) acryloxy propyl sulfonic acid, 2-hydroxy-3-(meth) acryloxy propyl sulfonic acid, 2-(meth) acryloylamino-2,2-dimethylethane sulfonic acid, 3-(meth) acryloxyethane sulfonic acid, 2-(meth) acrylamide-2-methylpropane sulfonic acid, and 3-(meth) acrylamide-2-hydroxypropane sulfonic acid; and alkyl (meth) allyl sulfosuccinate.

Examples of a water-soluble ethylenically unsaturated monomer having a sulfoxy group and/or a salt thereof include sulfate ester of hydroxyalkyl (meth) acrylate; and sulfate ester of polyoxyalkylene mono(meth) acrylate.

Examples of a water-soluble ethylenically unsaturated monomer having a phosphono group and/or a salt thereof include phosphate monoesters of (meth) acrylic acid hydroxyalkyl, phosphate diesters of (meth) acrylic acid hydroxyalkyl, and (meth) acrylic acid alkylphosphonic acids.

Examples of a water-soluble ethylenically unsaturated monomer having a hydroxyl group include mono-ethylenically unsaturated alcohols having 3 to 15 carbon atoms such as (meth) allyl alcohol and (meth) propenyl alcohol; mono-ethylenically unsaturated carboxylates or mono-ethylenically unsaturated ethers of bivalent to hexavalent polyols such as alkylene glycol having 2 to 20 carbon atoms, glycerin, sorbitan, diglycerin, pentaerythritol, and polyalkylene (2 to 4 carbon atoms) glycol (weight average molecular weight: 100 to 2000). Specific examples of them include hydroxyethyl (meth) acrylate, hydroxypropyl (meth) acrylate, triethyleneglycol (meth) acrylate, and poly-oxyethylene-oxypropylene mono (meth) allyl ether.

Examples of a water-soluble ethylenically unsaturated monomer having a carbamoyl group include (meth) acrylamide; N-alkyl (1 to 8 carbon atoms) (meth) acrylamides such as N-methyl acrylamide; N, N-dialkyl (alkyl having 1 to 8 carbon atoms) acrylamides such as N. N-dimethyl acrylamide and N, N-di-n- or i-propyl acrylamide; N-hydroxyalkyl (1 to 8 carbon atoms) (meth) acrylamides such as N-methylol (meth) acrylamide and N-hydroxyethyl (meth) acrylamide; and N,N-dihydroxyalkyl (1 to 8 carbon atoms) (meth) acrylamides such as N,N-dihydroxyethyl (meth) acrylamide. As an unsaturated monomer having a group composed of an amide, in addition to them, vinyl lactams having 5 to 10 carbon atoms (N-vinyl pyrrolidone, etc.) and the like can also be used.

Examples of a water-soluble ethylenically unsaturated monomer having an amino group include an amino group-containing ester of a mono-ethylenically unsaturated mono- or di-carboxylic acid and an amino group-containing amide of a mono-ethylenically unsaturated mono- or di-carboxylic acid. As the amino group-containing ester of a mono-ethylenically unsaturated mono- or di-carboxylic acid, dialkylaminoalkyl (meth) acrylate, di(hydroxyalkyl) aminoalkyl ester, morpholinoalkyl ester, and the like can be used, and examples thereof include dimethylaminoethyl (meth) acrylate, diethylamino (meth) acrylate, morpholinoethyl (meth) acrylate, dimethylaminoethyl fumarate, and dimethylaminoethyl malate. As the amino group-containing amide of a mono-ethylenically unsaturated mono- or di-carboxylic acid, monoalkyl (meth) acrylamide is preferred, and examples thereof include dimethylaminoethyl (meth) acrylamide and diethylaminoethyl (meth) acrylamide. As the water-soluble ethylenically unsaturated monomer having an amino group, in addition to them, vinylpyridines such as 4-vinylpyridine and 2-vinylpyridine can also be used.

The hydrolyzable monomer (a2) producing the water-soluble ethylenically unsaturated monomer (a1) by hydrolysis is not particularly limited, but an ethylenically unsaturated monomer having at least one hydrolyzable substituent that becomes a water-soluble substituent by hydrolysis is preferred. Examples of the hydrolyzable substituent include a group containing an acid anhydride, a group containing an ester linkage, and a cyano group.

As an ethylenically unsaturated monomer having a group containing an acid anhydride, an unsaturated dicarboxylic anhydride having 4 to 20 carbon atoms is used, and examples thereof include maleic anhydride, itaconic anhydride, and citraconic anhydride. Examples of an ethylenically unsaturated monomer having a group containing an ester linkage include lower alkyl esters of mono-ethylenically unsaturated carboxylic acids such as methyl (meth) acrylate and ethyl (meth) acrylate; and esters of mono-ethylenically unsaturated alcohols such as vinyl acetate and (meth) allyl acetate. Examples of an ethylenically unsaturated monomer having a cyano group include vinyl group-containing nitrile compounds having 3 to 6 carbon atoms such as (meth) acrylonitrile and 5-hexenenitrile.

As the water-soluble ethylenically unsaturated monomer (a1) and the hydrolyzable monomer (a2), those described in Japanese Patent No. 3648553 B, Japanese Patent Publication No. 2003-165883 A, Japanese Patent Publication No. 2005-75982 A, and Japanese Patent Publication No. 2005-95759 A can be further used.

As each of the water-soluble ethylenically unsaturated monomer (a1) and the hydrolyzable monomer (a2), a single monomer or a mixture of two or more monomers may be used. The same applies to the case where the water-soluble ethylenically unsaturated monomer (a1) and the hydrolyzable monomer (a2) are used in combination. In addition, when the water-soluble ethylenically unsaturated monomer (a1) and the hydrolyzable monomer (a2) are used in combination, the molar content ratio (a1/a2) of them is preferably from 75/25 to 99/1, more preferably from 85/15 to 95/5, even more preferably from 90/10 to 93/7, and most preferably from 91/9 to 92/8. When the molar content ratio falls within the above range, the absorbing performance becomes further preferable.

As the monomer constituting the crosslinked polymer (A), in addition to the water-soluble ethylenically unsaturated monomer (a1) and the hydrolyzable monomer (a2), another vinyl monomer (a3) that is copolymerizable with these monomers can be used. As the copolymerizable other vinyl monomer (a3), hydrophobic vinyl monomers and the like can be used, but it is not limited to them. As the other vinyl monomer (a3), the following vinyl monomers (i) to (iii) and the like are used.

(i) Aromatic ethylenically unsaturated monomers having 8 to 30 carbon atoms;

Styrenes such as styrene, alpha-methylstyrene, vinyltoluene, and hydroxystyrene; vinylnaphthalene; and halogen substitutions of styrene such as dichlorostyrene.

(ii) Aliphatic ethylenically unsaturated monomers having 2 to 20 carbon atoms;

Alkenes such as ethylene, propylene, butene, isobutylene, pentene, heptene, diisobutylene, octene, dodecene, and octadecene; and alkadienes such as butadiene, and isoprene.

(iii) Alicyclic ethylenically unsaturated monomers having 5 to 15 carbon atoms;

Mono-ethylenically unsaturated monomers such as pinene, limonene, and indene; and polyethylenic vinyl-polymerizable monomers such as cyclopentadiene, bicyclopentadiene, and ethylidene norbornene.

As the other vinyl monomer (a3), those described in Japanese Patent No. 3648553 B, Japanese Publication No. 2003-165883 A, Japanese Patent Publication No. 2005-75982 A, and Japanese Patent Publication No. 2005-95759 A can be further used.

When the other vinyl monomer (a3) is used, the content (mole %) of the other vinyl monomer (a3) with respect to the total amount (100 mole %) of the water-soluble ethylenically unsaturated monomer (a1) and the hydrolyzable monomer (a2) is preferably 0.01 mole % to 5 mole %, more preferably 0.05 mole % to 3 mole %, even more preferably 0.08 mole % to 2 mole %, and most preferably 0.1 mole % to 1.5 mole %. It is noted that in light of absorption properties, the content of the other vinyl monomer (a3) is most preferably 0 mole %.

Examples of the internal crosslinking agent (b) can include an internal crosslinking agent (b1) having two or more ethylenically unsaturated groups, an internal crosslinking agent (b2) having: at least one functional group that can react with a water-soluble substituent of the water-soluble ethylenically unsaturated monomer (a1) and/or a water-soluble substituent produced by hydrolysis of the hydrolyzable monomer (a2); and at least one ethylenically unsaturated group, and an internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2).

Examples of the internal crosslinking agent (b1) having two or more ethylenically unsaturated groups include bis (meth) acrylamides having 8 to 12 carbon atoms, poly (meth) acrylates of polyols having 2 to 10 carbon atoms, polyallylamines having 2 to 10 carbon atoms, and poly (meth) allyl ethers of polyols having 2 to 10 carbon atoms. Specific examples of them include N,N'-methylene bis (meth) acrylamide, ethylene glycol di(meth) acrylate, poly (polymerization degree of 2 to 5) ethylene glycol di(meth) acrylate, propylene glycol di(meth) acrylate, glycerol (di or tri) acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth) acrylate.

Examples of the internal crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group include ethylenically unsaturated compounds having 6 to 8 carbon atoms and an epoxy group, ethylenically unsaturated compounds having 4 to 8 carbon atoms and a hydroxyl group, and ethylenically unsaturated compounds having 4 to 8 carbon atoms and an isocyanato group. Specific examples of them include glycidyl (meth) acrylate, N-methylol (meth) acrylamide, hydroxyethyl (meth) acrylate, and isocyanato ethyl (meth) acrylate.

Examples of the internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2) can include polyhydric alcohols, polyvalent glycidyls, polyvalent amines, polyvalent aziridines, and polyvalent isocyanates. Examples of polyvalent glycidyl compounds include ethylene glycol diglycidyl ether and glycerin diglycidyl ether. Examples of polyvalent amine compounds include ethylenediamine, diethylenetriamine, triethylenetetramine, tetraethylenepentamine, pentaethylenehexamine, and polyethyleneimine. Examples of polyvalent aziridine compounds include Chemitite (registered trademark) PZ-33 {2,2-bishydroxymethylbutanol-tris (3-(1-aziridinyl) propionate)}, Chemitite HZ-22 {1,6-hexamethylenediethyleneurea}, and Chemitite DZ-22 {diphenylmethane-bis-4,4'-N,N'-diethyleneurea}, available from Nippon Shokubai Co., Ltd. Examples of polyvalent polyisocyanate compounds include 2,4-tolylene diisocyanate and hexamethylene diisocyanate. These internal crosslinking agents may be used singly or two or more of them may be used in combination.

As the internal crosslinking agent (b), in light of absorbing performance (in particular, an absorption amount, an absorption speed, etc.), the internal crosslinking agent (b1) having two or more ethylenically unsaturated groups is preferred, poly (meth) allyl ethers of polyols having 2 to 10 carbon atoms are more preferred, triallylcyanurate, triallylisocyanurate, tetraallyloxyethane, or pentaerythritol triallyl ether is further preferred, and pentaerythritol triallyl ether is most preferred.

As the internal crosslinking agent (b), those described in Japanese Patent No. 3648553 B, Japanese Patent Publication No. 2003-165883 A, Japanese Patent Publication No. 2005-75982 A, and Japanese Patent Publication No. 2005-95759 A can be further used.

The content (mole %) of the internal crosslinking agent (b) with respect to the total amount (100 mole %) of the water-soluble ethylenically unsaturated monomer (a1) and the hydrolyzable monomer (a2) is preferably from 0.001 mole % to 5 mole %, more preferably from 0.005 mole % to 3 mole %, and even more preferably from 0.01 mole % to 1 mole %. When the content falls within this range, the absorbing performance (in particular, an absorption amount, an absorption speed, etc.) becomes further favorable.

As the method for polymerizing the crosslinked polymer (A), a conventionally known method and the like can be used, and a solution polymerization method, an emulsion polymerization method, a suspension polymerization method, and a reversed-phase suspension polymerization method can be used. In addition, a polymerization liquid at the polymerization may be in the form of a thin film, mist, or the like. As the method for controlling the polymerization, an adiabatic polymerization method, a temperature-controlled polymerization method, an isothermal polymerization method, and the like can be used.

When the suspension polymerization method or the reversed-phase suspension polymerization method is employed as the polymerization method, conventionally known dispersants such as sucrose esters, phosphates, and sorbitan esters, protective colloids such as poval, alpha-olefin-maleic anhydride copolymers, and oxidized polyethylene, and the like can be used where necessary. In addition, in the case with the reversed-phase suspension polymerization method, polymerization can be conducted by using a solvent such as cyclohexane, normal hexane, normal heptane, toluene, and xylene. As the polymerization method, the solution polymerization method is preferred, and an aqueous solution polymerization method is more preferred since an organic solvent and the like are not used and it is advantageous in terms of production cost.

A water-containing gel (consisting of the crosslinked polymer and water) obtained by the polymerization can be chopped where necessary. The size (largest diameter) of the chopped gel is preferably from 50 μm to 10 cm, more preferably from 100 μm to 2 cm, and even more preferably from 1 mm to 1 cm. If the size falls within this range, dryability at a drying process becomes further favorable.

The chopping can be conducted by a known method, and can be conducted, for example, by using a conventional chopping apparatus such as a Bexmill, a rubber chopper, a Pharma Mill, a mincing machine, an impact type mill, and a roll type mill.

When a solvent (an organic solvent, water, etc.) is used for the polymerization, it is preferred to remove the solvent by distillation after the polymerization. When the solvent contains an organic solvent, the content (mass %) of the organic solvent with respect to the mass (100 mass %) of the crosslinked polymer after the removal by distillation is preferably from 0 mass % to 10 mass %, more preferably from 0 mass % to 5 mass %, even more preferably from 0 mass % to 3 mass %, and most preferably from 0 mass % to 1 mass %. When the content of the organic solvent falls within the above range, the absorbing performance (in particular, water retaining capacity) of the water absorbent resin powder becomes further favorable.

When the solvent contains water, the water content (mass %) with respect to the mass (100 mass %) of the crosslinked polymer after the removal by distillation is preferably from 0 mass % to 20 mass %, more preferably from 1 mass % to 10 mass %, even more preferably from 2 mass % to 9 mass %, and most preferably from 3 mass % to 8 mass %. When the water content (% by mass) falls within the above range, the absorbing performance and the breakability of the water absorbent resin powder after drying become further favorable.

It is noted that the content of the organic solvent and the water content are obtained based on a decrease in the mass of a measurement sample from before heating to after heating by an infrared moisture measuring instrument {"JE400" manufactured by Kett Electric Laboratory or the like: 120 plus or minus 5 degrees centigrade, 30 minutes, an atmospheric humidity before heating of 50 plus or minus 10% RH, lamp specifications of 100 V and 40 W}.

As the method for removing the solvent (including water) by distillation, a method in which removal by distillation (drying) is conducted by hot air at a temperature in a range from 80 degrees centigrade to 230 degrees centigrade, a thin film drying method with a drum dryer or the like heated at the temperature in a range from 100 degrees centigrade to 230 degrees centigrade, a (heating) reduced-pressure drying method, a freeze-drying method, a drying method with infrared rays, decantation, filtration, and the like can be used.

The crosslinked polymer (A) can be pulverized after being dried. The pulverizing method is not particularly limited, and, for example, an ordinary pulverizing apparatus such as a hammer type pulverizer, an impact type pulverizer, a roll type pulverizer, and a jet streaming type pulverizer can be used. The particle size of the pulverized crosslinked polymer (A) can be adjusted by sieving or the like where necessary.

The weight average particle size (μm) of the crosslinked polymer (A) that is sieved where necessary is preferably from 100 μm to 800 μm, more preferably from 200 μm to 700 μm, even more preferably from 250 μm to 600 μm, particularly preferably from 300 μm, to 500 μm, and most preferably from 350 μm to 450 μm. If the weight average particle size (μm) of the crosslinked polymer (A) falls within the above range, the absorbing performance becomes further favorable.

It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21). In other words, as JIS standard sieves, for example, sieves of 1000 μm, 850 μm, 710 μm, 500 μm, 425 μm, 355 μm, 250 μm, 150 μm, 125 μm, 75 μm, and 45 μm, and a tray are combined in order from above. About 50 g of a measurement particle is placed into the uppermost sieve, and shaken with the ro-tap test sieve shaker for 5 minutes. The masses of the measurement particles on each sieve and the tray are measured, and the mass fraction of the particles on each sieve is obtained with the total mass regarded as 100% by mass. The values are plotted in a log probability paper (the horizontal axis is used for the opening of the sieve (particle size) and the vertical axis is used for the mass fraction), then a line is drawn so as to connect each point, and a particle size corresponding to 50% by mass of the mass fraction is obtained and regarded as a weight average particle size.

In addition, the lower the content of fine particles is, the more favorable the absorbing performance becomes. Thus, the content of fine particles having a size of 106 μm or less (preferably, 150 μm or less) in the entire particles is preferably 3 mass % or less, and even more preferably 1 mass % or less. The content of fine particles can be obtained by using the plot created when the above weight average particle size is obtained.

The crosslinked polymer (A) may be one polymer or a mixture of two or more polymers.

Examples of the surface modifier (B) include polyvalent metal compounds such as aluminum sulfate, potassium alum, ammonium alum, sodium alum, (poly) aluminum chloride, and hydrates thereof; polycation compounds such as polyethyleneimine, polyvinylamine, and polyallylamine; inorganic fine particles; a surface modifier (B1) containing a hydrocarbon group; a surface modifier (B2) containing a hydrocarbon group having a fluorine atom; and a surface modifier (B3) having a polysiloxane structure.

Examples of the inorganic fine particles include oxides such as silicon oxide, aluminum oxide, iron oxide, titanium oxide, magnesium oxide, and zirconium oxide, carbides such as silicon carbide and aluminum carbide, nitrides such as titanium nitride, and complexes thereof (e.g., zeolite, talc, etc.). Among them, oxides are preferred, and silicon oxide is further preferred. The volume average particle size of the inorganic fine particles is preferably from 10 nm to 5000 nm, more preferably from 30 nm to 1000 nm, even more preferably from 50 nm to 750 nm, and most preferably from 90 nm to 500 nm. It is noted that the volume average particle size is measured in a solvent by a dynamic light scattering method. Specifically, the volume average particle size is measured in cyclohexane as a solvent at a temperature of 25 degrees centigrade by using the nano track particle size distribution measuring instrument UPA-EX150 (light source: He—Ne laser) manufactured by Nikkiso Co., Ltd.

The specific surface area of the inorganic fine particles are preferably in a range of 20 $m^2/g$ to 400 $m^2/g$, more preferably in a range of 30 $m^2/g$ to 350 $m^2/g$, and even more preferably in a range of 40 $m^2/g$ to 300 $m^2/g$. If the specific surface area falls within this range, the absorbing performance becomes further favorable. It is noted that the specific surface area is measured according to JIS Z8830: 2001 (nitrogen, a volume method, a multipoint method).

The inorganic fine particles are commercially easily available. Examples thereof (hereinafter, trade name (chemical composition, volume average particle size nm, specific surface area $m^2/g$)) include Aerosil (registered trademark) 130 (silicon dioxide, 16, 130), Aerosil 200 (silicon dioxide, 12, 200), Aerosil 300 (silicon dioxide, 7, 300), Aerosil MOX80 (silicon dioxide, 30, 80), Aerosil COK84 (silicon dioxide, 12, 170), Aerosil OX50T (silicon dioxide, 7, 40), titanium oxide P25 (titanium oxide, 20, 30), and Aluminum Oxide C (aluminum oxide, 13, 100) {Nippon Aerosil Co., Ltd.}; Denka Fused Silica F-300 (silicon dioxide, 11, 160) {Denki Kagaku Kogyo Kabushiki Kaisha}; Microd 850 (silicon dioxide, 13, 150) {Tokai Chemical Industry Co., Ltd.}; Amorphous Silica SP-1 (silicon dioxide, 14, 45) {Nozawa Corporation}; Syloid 622 (silicon dioxide, 17, 350) and Syloid ED50 (silicon dioxide, 8, 400) {Grace Japan Co., Ltd.}; Admafine SO-C1 (complex oxide, 0.1, 20) {Admatechs Company Limited}; Tokusil (silicon dioxide, 2.5, 120) and Reolosil (registered trademark) (silicon dioxide, 2.5, 110) {Tokuyama Corporation}; Nipsil E220A (silicon dioxide, 2.5, 130) {Nihon Silica Kogyo K.K.}; and Klebosol 30CAL25 (silicon oxide, 12, 200) {Clariant (Japan) K.K.}.

Examples of the surface modifier (B1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, and mixtures of two or more of them.

Examples of polyolefin resins include a polymer that is obtained by polymerizing an olefin having 2 to 4 carbon atoms such as ethylene, propylene, isobutylene, and isoprene and has a weight average molecular weight from 1,000 to 1,000,000. The content of the olefin component in the polymer is preferably at least 50 mass % in 100% by mass of the polyolefin resin. Specific examples of polyolefin resins include polyethylene, polypropylene, polyisobutylene, poly (ethylene-isobutylene), and isoprene.

As a polyolefin resin derivative, a polymer that has a weight average molecular weight of 1,000 to 1,000,000 and in which a carboxy group (—COOH), 1,3-oxo-2-oxapropylene (—COOCO—), or the like is introduced into a polyolefin resin is preferred. Specific examples thereof include polyethylene thermal degradation products, polypropylene thermal degradation products, maleic acid-modified polyethylene, chlorinated polyethylene, maleic acid-modified polypropylene, ethylene-acrylic acid copolymers, ethylene-maleic anhydride copolymers, isobutylene-maleic anhydride copolymers, maleinated polybutadiene, ethylene-vinyl acetate copolymers, and maleinated products of ethylene-vinyl acetate copolymers.

As a polystyrene resin, a polymer having a weight average molecular weight of 1,000 to 1,000,000 and the like can be used.

As a polystyrene resin derivative, a polymer that contains styrene as an essential constituent monomer and has a weight average molecular weight of 1,000 to 1,000,000 is preferred. The content of styrene is preferably at least 50 mass % in 100 mass % of the polystyrene derivative. Specific examples of polystyrene resin derivatives include styrene-maleic anhydride copolymers, styrene-butadiene copolymers, and styrene-isobutylene copolymers.

Examples of waxes include waxes having a melting point of 50 degrees centigrade to 200 degrees centigrade such as paraffin wax, bees wax, carnauba wax, and beef tallow.

As a long-chain fatty acid ester, an ester of a fatty acid having 8 to 30 carbon atoms and an alcohol having 1 to 12 carbon atoms is preferred. Specific examples of long-chain fatty acid esters include methyl laurate, ethyl laurate, methyl stearate, ethyl stearate, methyl oleate, ethyl oleate, glycerin laurate monoester, glycerin stearate monoester, glycerin oleate monoester, pentaerythritol laurate monoester, pentaerythritol stearate monoester, pentaerythritol oleate monoester, sorbitol laurate monoester, sorbitol stearate monoester, sorbitol oleate monoester, sucrose palmitate monoester, sucrose palmitate diester, sucrose palmitate triester, sucrose stearate monoester, sucrose stearate diester, sucrose stearate triester, and beef tallow. Among them, in light of leakage resistance of the absorbent article, sucrose stearate monoester, sucrose stearate diester, and sucrose stearate triester are preferred, and sucrose stearate monoester and sucrose stearate diester are further preferred.

As a long-chain fatty acid and a salt thereof, a fatty acid having 8 to 30 carbon atoms and a salt thereof are preferred. Examples of fatty acids having 8 to 30 carbon atoms include lauric acid, palmitic acid, stearic acid, oleic acid, dimer acid, and behenic acid. As a metal component of a salt of the fatty acid having 8 to 30 carbon atoms, for example, zinc, calcium, magnesium, or aluminum (hereinafter, they are abbreviated as Zn, Ca, Mg, and Al) is preferred. Specific examples of salts of fatty acids having 8 to 30 carbon atoms include Ca palmitate, Al palmitate, Ca stearate, Mg stearate, and Al stearate. In light of leakage resistance of the absorbent article, as the long-chain fatty acid and a salt thereof, Zn stearate, Ca stearate, Mg stearate, and Al stearate are preferred, and Mg stearate is more preferred.

Examples of long-chain aliphatic alcohols include aliphatic alcohols having 8 to 30 carbon atoms such as lauryl alcohol, palmityl alcohol, stearyl alcohol, and oleyl alcohol. In light of leakage resistance of the absorbent article, as the long-chain aliphatic alcohol, palmityl alcohol, stearyl alcohol, and oleyl alcohol are preferred, and stearyl alcohol is further preferred.

Examples of the surface modifier (B2) containing a hydrocarbon group having a fluorine atom include perfluoroalkanes, perfluoroalkenes, perfluoroaryls, perfluoroalkyl ethers, perfluoroalkylcarboxylic acids or salts thereof, perfluoroalkyl alcohols, and mixtures of two or more of them.

As a perfluoroalkane, an alkane having 4 to 42 fluorine atoms and 1 to 20 carbon atoms is preferred. Examples of perfluoroalkanes include trifluoromethane, pentafluoroethane, pentafluoropropane, heptafluoropropane, heptafluorobutane, nonafluorohexane, tridecafluorooctane, and heptadecafluorododecane.

As a perfluoroalkene, an alkene having 4 to 42 fluorine atoms and 2 to 20 carbon atoms is preferred. Examples of perfluoroalkenes include trifluoroethylene, pentafluoropropene, trifluoropropene, heptafluorobutene, nonafluorohexene, tridecafluorooctene, and heptadecafluorododecene.

As a perfluoroaryl, an aryl having 4 to 42 fluorine atoms and 6 to 20 carbon atoms is preferred. Examples of perfluoroaryls include trifluorobenzene, pentafluorotoluene, trifluoronaphthalene, heptafluorobenzene, nonafluoroxylene, tridecafluorooctylbenzene, and heptadecafluorododecylbenzene.

As a perfluoroalkyl ether, an ether having 2 to 82 fluorine atoms and 2 to 40 carbon atoms is preferred. Examples of perfluoroalkyl ethers include ditrifluoromethyl ether, dipentafluoroethyl ether, dipentafluoropropyl ether, diheptafluoropropyl ether, diheptafluorobutyl ether, dinonafluorohexyl ether, ditridecafluorooctyl ether, and diheptadecafluorododecyl ether.

As a perfluoroalkylcarboxylic acid or a salt thereof, a carboxylic acid having 3 to 41 fluorine atoms and 1 to 21 carbon atoms or a salt thereof is preferred. Examples of perfluoroalkylcarboxylic acids or salts thereof include pentafluoroethanoic acid, pentafluoropropanoic acid, heptafluoropropanoic acid, heptafluorobutanoic acid, nonafluorohexanoic acid, tridecafluorooctanoic acid, heptadecafluorododecanoic acid, or metal salts thereof. As a metal salt, an alkali metal salt or an alkaline earth metal salt is preferred.

As a perfluoroalkyl alcohol, an alcohol having 3 to 41 fluorine atoms and 1 to 20 carbon atoms is preferred. Examples of perfluoroalkyl alcohols include pentafluoroethanol, pentafluoropropanol, heptafluoropropanol, heptafluorobutanol, nonafluorohexanol, tridecafluorooctanol, heptadecafluorododecanol, and ethylene oxide (1 to 20 mol per 1 mol of alcohol) adducts of these alcohols.

Examples of mixtures of two or more of them include a mixture of a perfluoroalkylcarboxylic acid and a perfluoroalkyl alcohol, and, for example, a mixture of pentafluoroethanoic acid and pentafluoroethanol is preferred.

Examples of the surface modifier (B3) having a polysiloxane structure include polydimethylsiloxane; polyether-modified polysiloxanes such as polyoxyethylene-modified polysiloxane and poly (oxyethylene/oxypropylene)-modified polysiloxane; carboxy-modified polysiloxanes; epoxy-modified polysiloxanes: amino-modified polysiloxanes; alkoxy-modified polysiloxanes; and mixtures thereof.

The position of an organic group (modifying group) of a modified silicone such as polyether-modified polysiloxanes, carboxy-modified polysiloxanes, epoxy-modified polysiloxanes, and amino-modified polysiloxanes is not particularly limited, but the position of the organic group may be a side chain of the polysiloxane, both terminals of the polysiloxane, one terminal of the polysiloxane, or combination of a side chain and both terminals of the polysiloxane. Among them, in light of absorption properties, the position is preferably either a side chain of the polysiloxane or combination of a side chain and both terminals of the polysiloxane, and more preferably combination of a side chain and both terminals of the polysiloxane.

Examples of an organic group (modified group) of a polyether-modified polysiloxane include groups containing a polyoxyethylene chain or a poly (oxyethylene-oxypropylene) chain. The number of the oxyethylene units and/or oxypropylene units contained in the polyether-modified polysiloxane is preferably from 2 to 40, more preferably from 5 to 30, even more preferably from 7 to 20, and most preferably from 10 to 15 per one polyether-modified polysiloxane molecule. When the number falls within this range, the absorption properties become further favorable. Also, in the case where an oxyethylene group and an oxypropylene group are contained, the content (mass %) of the oxyethylene group and the oxypropylene group in 100 mass % of the polyether-modified polysiloxane is preferably from 1 mass % to 30 mass %, more preferably from 3 mass % to 25 mass %, and even more preferably from 5 mass % to 20 mass %. When the content of the oxyethylene group and the oxypropylene group falls within the above range, the absorption properties become further favorable.

The polyether-modified polysiloxanes are commercially easily available and, for example, the following commercial products {modification position, type of oxyalkylene} can be preferably exemplified.

Products manufactured by Shin-Etsu Chemical Co., Ltd: KF-945 {side chain, oxyethylene and oxypropylene}, KF-6020 {side chain, oxyethylene and oxypropylene}, X-22-6191 {side chain, oxyethylene and oxypropylene}, X-22-4952 {side chain, oxyethylene and oxypropylene}, X-22-4272 {side chain, oxyethylene and oxypropylene}, and X-22-6266 {side chain, oxyethylene and oxypropylene}.

Products manufactured by Dow Corning Toray Co., Ltd: FZ-2110 {both terminals, oxyethylene and oxypropylene}, FZ-2122 {both terminals, oxyethylene and oxypropylene}, FZ-7006 {both terminals, oxyethylene and oxypropylene}, FZ-2166 {both terminals, oxyethylene and oxypropylene}, FZ-2164 {both terminals, oxyethylene and oxypropylene}, FZ-2154 {both terminals, oxyethylene and oxypropylene}, FZ-2203 {both terminals, oxyethylene and oxypropylene}, and FZ-2207 {both terminals, oxyethylene and oxypropylene}.

Examples of an organic group (modifying group) of a carboxy-modified polysiloxanes include groups containing a carboxy group, examples of an organic group (modifying group) of an epoxy-modified polysiloxane include groups containing an epoxy group, and examples of an organic group (modifying group) of an amino-modified polysiloxane include groups containing an amino group (primary, secondary, or tertiary amino group). The content (g/mol) of the organic group (modifying group) in each of these modified silicones is preferably from 200 to 11,000, more preferably from 600 to 8,000, and even more preferably from 1,000 to 4,000, as a carboxy equivalent, an epoxy equivalent, or an amino equivalent. If the content falls within this range, the absorption properties become further favorable. It is noted that the carboxy equivalent is measured according to "16. Total Acid Value Test" of JIS C2101: 1999. Also, the epoxy equivalent is obtained according to JIS K7236: 2001. Moreover, the amino equivalent is measured according to "8. Potentiometric Titration (base value-hydrochloric acid method)" of JIS K2501: 2003.

The carboxy-modified polysiloxanes are commercially easily available and, for example, the following commercial products {modification position, carboxy equivalent (g/mol)} can be preferably exemplified.

Products manufactured by Shin-Etsu Chemical Co., Ltd.: X-22-3701E {side chain, 4000}, X-22-162C {both terminals, 2300}, and X-22-3710 {one terminal, 1450}.

Products manufactured by Dow Corning Toray Co., Ltd.: BY 16-880 {side chain, 3500}, BY 16-750 {both terminals, 750}, BY 16-840 {side chain, 3500}, and SF8418 {side chain, 3500}.

The epoxy-modified polysiloxanes are commercially easily available and, for example, the following commercial products {modification position, epoxy equivalent} can be preferably exemplified.

Products manufactured by Shin-Etsu Chemical Co., Ltd.: X-22-343 {side chain, 525}, KF-101 {side chain, 350}, KF-1001 {side chain, 3500}, X-22-2000 {side chain, 620}, X-22-2046 {side chain, 600}, KF-102 {side chain, 3600}, X-22-4741 {side chain, 2500}, KF-1002 {side chain, 4300}, X-22-3000T {side chain, 250}, X-22-163 {both terminals, 200}, KF-105 {both terminals, 490}, X-22-163A {both terminals, 1000}, X-22-163B {both terminals, 1750}, X-22-163C {both terminals, 2700}, X-22-169AS {both terminals, 500}, X-22-169B {both terminals, 1700}, X-22-173DX {one terminal, 4500}, and X-22-9002 {side chain and both terminals, 5000}.

Products manufactured by Dow Corning Toray Co., Ltd.: FZ-3720 {side chain, 1200}, BY 16-839 {side chain, 3700}, SF 8411 {side chain, 3200}, SF 8413 {side chain, 3800}, SF 8421 {side chain, 11000}, BY 16-876 {side chain, 2800}, FZ-3736 {side chain, 5000}, BY 16-855D {side chain, 180}, and BY 16-8 {side chain, 3700}.

The amino-modified silicones are commercially easily available and, for example, the following commercial products {modification position, amino equivalent} can be preferably exemplified.

Products manufactured by Shin-Etsu Chemical Co., Ltd.: KF-865 {side chain, 5000}, KF-864 {side chain, 3800}, KF-859 {side chain, 6000}, KF-393 {side chain, 350}, KF-860 {side chain, 7600}, KF-880 {side chain, 1800}, KF-8004 {side chain, 1500}, KF-8002 {side chain, 1700}, KF-8005 {side chain, 11000}, KF-867 {side chain, 1700}, X-22-3820W {side chain, 55000}, KF-869 {side chain, 8800}, KF-861 {side chain, 2000}, X-22-3939A {side chain, 1500}, KF-877 {side chain, 5200}, PAM-E {both terminals, 130}, KF-8010 {both terminals, 430}, X-22-161A {both terminals, 800}, X-22-161B {both terminals, 1500}, KF-8012 {both terminals, 2200}, KF-8008 {both terminals, 5700}, X-22-1660B-3 {both terminals, 2200}, KF-857 {side chain, 2200}, KF-8001 {side chain, 1900}, KF-862 {side chain, 1900}, and X-22-9192 {side chain, 6500}.

Products manufactured by Dow Corning Toray Co., Ltd.: FZ-3707 {side chain, 1500}, FZ-3504 {side chain, 1000}, BY 16-205 {side chain, 4000}, FZ-3760 {side chain, 1500}, FZ-3705 {side chain, 4000}, BY 16-209 {side chain, 1800}, FZ-3710 {side chain, 1800}, SF 8417 {side chain, 1800}. BY 16-849 {side chain, 600}, BY 16-850 {side chain, 3300}, BY 16-879B {side chain, 8000}, BY 16-892 {side chain, 2000}, FZ-3501 {side chain, 3000}, FZ-3785 {side chain, 6000}, BY 16-872 {side chain, 1800}, BY 16-213 {side chain, 2700}, BY 16-203 {side chain, 1900}, BY 16-898 {side chain, 2900}, BY 16-890 {side chain, 1900}, BY 16-893 {side chain, 4000}, FZ-3789 {side chain, 1900}, BY 16-871 {both terminals, 130}, BY 16-853C {both terminals, 360}, and BY 16-853U {both terminals, 450}.

Examples of mixtures of them include a mixture of polydimethylsiloxane and a carboxyl-modified polysiloxane, and a mixture of a polyether-modified polysiloxane and an amino-modified polysiloxane.

As the surface modifier (B), in light of absorption properties, the surface modifier (B3) having a polysiloxane structure and inorganic fine particles are preferred, amino-modified polysiloxanes, carboxy-modified polysiloxanes, and silica are more preferred.

The method for treating the crosslinked polymer (A) with the surface modifier (B) is not particularly limited, as long as treatment is conducted such that the surface modifier (B) is present on the surface of the crosslinked polymer (A). However, from the standpoint that the amount of the surface modifier (B) on the surface is controlled, it is preferred that the surface modifier (B) is mixed with a dried product of the crosslinked polymer (A), not with a water-containing gel of the crosslinked polymer (A) or a polymerization liquid that is prior to polymerization of the crosslinked polymer (A). It is noted that it is preferred that the mixing is uniformly conducted.

An amount of the surface modifier (B) for the treatment preferably ranges from 0.001 part by mass to 1 part by mass with respect to 100 parts by mass of the crosslinked polymer (A).

The shape of the water absorbent resin powder is not particularly limited, and examples thereof include an indefinite crushed shape, a scale shape, a pearl shape, and a rice grain shape. Among them, the indefinite crushed shape is preferred from the standpoint that the powder in such a shape can be well entangled with fibrous materials in applications such as a disposable diaper and there is little possibility of the powder falling off from the fibrous materials.

The water absorbent resin powder can be subjected to surface crosslinking where necessary. As a crosslinking agent for conducting the surface crosslinking (a surface crosslinking agent), the same ones as the internal crosslinking agent (b) can be used. In light of absorption performance and the like of the water absorbent resin powder, the surface crosslinking agent is preferably the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2), more preferably a polyvalent glycidyl, even more preferably ethylene glycol diglycidyl ether and glycerin diglycidyl ether, and most preferably ethylene glycol diglycidyl ether.

In the case of conducting the surface crosslinking, the content (mass %) of the surface crosslinking agent with respect to the total mass (100 mass %) of the water-soluble ethylenically unsaturated monomer (a1) and/or the hydrolyzable monomer (a2), the internal crosslinking agent (b), and the other vinyl monomer (a3) used where necessary is preferably from 0.001 mass % to 7 mass %, more preferably from 0.002 mass % to 5 mass %, and even more preferably 0.003 mass % to 4 mass %. In other words, in this case, the upper limit of the content of the surface crosslinking agent based on the total mass of (a1) and/or (a2), (b), and (a3) is preferably 7 mass %, more preferably 5 mass %, and even more preferably 4 mass %. Similarly, the lower limit is preferably 0.001 mass %, more preferably 0.002 mass %, and even more preferably 0.003 mass %. If the content of the surface crosslinking agent falls within the above range, the absorption performance becomes further favorable. The surface crosslinking can be achieved by, for example, a method of spraying an aqueous solution containing the surface crosslinking agent to the water absorbent resin powder or impregnating the water absorbent resin powder with the aqueous solution containing the surface crosslinking agent, followed by heating treatment (100 to 200 degrees centigrade) on the water absorbent resin powder.

The water absorbent resin powder can contain additives such as an antiseptic, a fungicide, an antibacterial, an antioxidant, a ultraviolet absorbent body, a coloring agent, a perfuming agent, a deodorizer, an inorganic powder, and an organic fibrous material. Examples of such additives include those exemplified in Japanese Patent Publication No. 2003-225565 A and Japanese Patent Publication No. 2006-131767 A. When these additives are contained, the content (mass %) of the additives with respect to the crosslinked polymer (A) (100 mass %) is preferably from 0.001 mass % to 10 mass %, more preferably from 0.01 mass % to 5 mass %, even more preferably from 0.05 mass % to 1 mass %, and most preferably from 0.1 mass % to 0.5 mass %.

The absorbent body may further include a water absorbent material such as a water absorbent fiber, in addition to the water absorbent resin powder. Examples of the water absorbent fiber include pulp fibers, cellulose fibers, rayon, and acetate fibers. The absorbent body may further include a fiber base material in addition to the water absorbent resin powder. Examples of the fiber base material include thermal bonding fibers and the like. Thermal bonding fibers are used to enhance shape retention. Specific examples of the thermal bonding fibers include polyolefin fibers such as polyethylene and polypropylene, polyester fibers, and composite fibers.

The absorbent body preferably comprises an air-laid water absorption layer obtained by an air laying method and including the water absorbent resin powder. The air laying method is, for example, a method of transporting a short fiber including an opened thermal bonding synthetic fiber while uniformly dispersing the short fiber in an air flow, letting the short fiber blown out of a screen having pores formed in a discharge part thereof fall on a metal or plastic net disposed below, and letting the short fiber be accumulated on the net while sucking the air below the net to produce the water absorption layer. The water absorbent resin powder may be accumulated on the plastic net together with the short fiber, or be applied on the web layer where only the short fiber is accumulated beforehand.

As described above, it is possible that, in the water absorption layer obtained by the air laying method, the short fiber is randomly three-dimensionally oriented to the width direction and thickness direction of the water absorption layer. Since the fibers are thermally bonded, delamination does not occur. Further, the water absorption layer obtained by the air laying method exhibits good uniformity, thus performance variability thereof also decreases.

The short fiber which can be used in the air-laid water absorption layer will be described. The short fiber is not particularly limited, and examples thereof include: a synthetic fiber such as polyester, acrylic polymer, acrylic-based polymer (vinyl chloride or vinylidene chloride copolymer), polyamide (nylon), vinylon, polypropylene, polyvinyl chloride, polyethylene, vinylidene, polyurethane, aramid, polyacrylate-based polymer, poly p-phenylenebenzobisoxazole (PBO), ethylenevinyl alcohol, acrylate and polylactic acid; a regenerated fiber such as rayon polynosic and cupra; a semi-synthetic fiber such as acetate, triacetate and promix; an inorganic fiber such as glass fiber, metal fiber and carbon fiber; and a natural fiber such as wool, cotton, hemp and pulp.

As the short fiber, a thermal bonding composite fiber is also preferably used. Examples of the thermal bonding composite fiber include: a core-sheath type in which a low-melting point component is used as the sheath component and a high-melting point component is used as the core component; and a side-by-side type in which one side is a low-melting point component and another side is a high-melting point component. Examples of the combination of two components for these composite short fibers include: PP (polypropylene)/PE (polyethylene), PET (polyethylene terephthalate)/PE, PP/low-melting point copolymeric PP, and PET/low-melting point copolymeric polyester. Herein, examples of the low-melting point copolymeric polyester include a modified copolymer having a basic structure of polyethylene terephthalate, polypropylene terephthalate, polybutylene terephthalate or the like, and modified with an aromatic dicarboxylic acid such as isophthalic acid and 5-metal sulfoisophthalic acid, an aliphatic dicarboxylic acid such as adipic acid and sebacic acid, or an aliphatic polyvalent alcohol such as diethylene glycol, propylene glycol and 1,4-butanediol. As the thermal bonding composite fiber, a side-by-side type or core-sheath type composite fiber, which is formed from polyethylene terephthalate/polyethylene, polypropylene/polyethylene, polypropylene/modified polyethylene or polypropylene/modified polypropylene, is preferable.

The melting point of the thermal bonding component which is a low-melting point component is preferably 80 degrees centigrade to 180 degrees centigrade, and more preferably 90 degrees centigrade to 160 degrees centigrade. If the melting point is less than 80 degrees centigrade, heat resistance of the fiber is low, thus trouble tends to occur during the manufacturing step. On the other hand, if the melting point is more than 180 degrees centigrade, it becomes necessary to increase the heat treatment temperature during the manufacturing step of the water absorption layer, thus productivity decreases.

The fiber length of the short fiber is preferably 0.4 mm to 20 mm, more preferably 0.6 mm to 10 mm, and even more preferably 1 mm to 4 mm. If the fiber length is less than 0.4 mm, the strength and rigity improvement effect is not sufficient. On the other hand, if the fiber length is more than 20 mm, the fibers are likely to tangle together, thus trouble tends to occur during the manufacturing step.

The short fiber may be crimped or not crimped, and may be a chopped strand. When the short fiber is crimped, a two-dimensional crimped fiber having a zigzag shape or a three-dimensional (steric) crimped fiber having a spiral shape, a ohm shape or the like, may be used.

In the air-laid water absorption layer, the mass per unit area of the water absorbent resin powder is preferably 150 g/m$^2$ or more, more preferably 200 g/m$^2$ or more, and even more preferably 400 g/m$^2$ or more, and is preferably 500 g/m$^2$ or less, more preferably 480 g/m$^2$ or less, and even more preferably 450 g/m$^2$ or less. If the mass per unit area is 150 g/m$^2$ or more, the absorption capacity of the air-laid water absorption layer further improves. If the mass per unit area is 500 g/m$^2$ or less, the texture of the absorbent body including the air-laid water absorption layer becomes better.

In addition, in the air-laid water absorption layer, the mass per unit area of the short fiber is preferably 15 g/m$^2$ or more, more preferably 30 g/m$^2$ or more, and even more preferably 50 g/m$^2$ or more, and is preferably 200 g/m$^2$ or less, more preferably 100 g/m$^2$ or less, and even more preferably 70 g/m$^2$ or less. If the mass per unit area is 15 g/m$^2$ or more, the strength of the air-laid water absorption layer further improves. If the mass per unit area is 200 g/m$^2$ or less, the texture of the absorbent body including the air-laid water absorption layer becomes better.

In the air-laid water absorption layer, the mass ratio of the water absorbent resin powder to a total mass of the air-laid water absorption layer is preferably 62.0 mass % or more, more preferably 77 mass % or more, and even more preferably 80 mass % or more, and is preferably 99.5 mass % or less, and more preferably 99 mass % or less. Because the air-laid water absorption layer is obtained by the air laying method, the content of the water absorbent resin powder can be increased as described above. As a result, the absorption capacity of the absorbent body can be further improved. The mass ratio of the water absorbent resin powder in the air-laid water absorption layer is calculated by the following equation.

$$\text{Mass ratio(mass \%)} = 100 \times \text{mass per unit area (g/m}^2\text{)} \\ \text{of water absorbent resin powder}/\{\text{mass per unit} \\ \text{area (g/m}^2\text{) of water absorbent resin powder} + \\ \text{mass per unit area (g/m}^2\text{) of short fiber}\}$$

The thickness of the water absorption layer is not particularly limited, but is preferably 4.9 mm or less, more preferably 2.9 mm or less, and even more preferably 1.9 mm or less. In addition, the mass per unit area of the water absorption layer is preferably 150 g/m$^2$ or more, more preferably 200 g/m$^2$ or more, and even more preferably 400 g/m$^2$ or more, and is preferably 500 g/m$^2$ or less, more preferably 480 g/m$^2$ or less, and even more preferably 450 g/m$^2$ or less. If the mass per unit area is 150 g/m$^2$ or more, the absorption capacity of the water absorption layer further improves. If the mass per unit area is 500 g/m$^2$ or less, the texture of the absorbent body including the water absorption layer becomes better.

The absorbent body preferably comprises a liquid permeable first sheet, a second sheet, and the water absorbent resin powder disposed between the first sheet and the second sheet. It is more preferable that the air-laid water absorption layer is disposed between the first sheet and the second sheet.

The first sheet is a sheet on the skin-contacting side and allows water in the body fluid from the wearer to readily pass therethrough. The liquid permeable first sheet is a liquid permeable sheet material and is preferably, for example, a nonwoven fabric formed from a hydrophilic fiber. The nonwoven fabric used as the first sheet is, for example, a point-bonded nonwoven fabric, an air-through nonwoven fabric, a spunlace nonwoven fabric, a spunbond nonwoven fabric, or an air-laid nonwoven fabric. As hydrophilic fibers forming these nonwoven fabrics, cellulose, rayon, cotton, and the like are used. It is noted that as the first sheet, a liquid permeable nonwoven fabric that is formed from a hydrophobic fiber (e.g., polypropylene, polyethylene, polyester, polyamide, and nylon) whose surface is hydrophilized with a surfactant may be used.

The second sheet may be either a liquid permeable sheet or a liquid impermeable sheet depending on the disposing embodiment of the absorbent body. As the liquid impermeable sheet, a water-repellent or liquid impermeable nonwoven fabric (e.g., a spunbond nonwoven fabric, a meltblown nonwoven fabric, and an SMS (spunbond-meltblown-spunbond) nonwoven fabric) formed from a hydrophobic fiber (e.g., polypropylene, polyethylene, polyester, polyamide, and nylon), or a water-repellent or liquid impermeable plastic film is used. The second sheet prevents the body fluid that reaches the liquid impermeable sheet, from oozing out of the absorbent body. If a plastic film is used as the liquid impermeable sheet, a moisture-permeable (air-permeable) plastic film is preferably used from the standpoint that humid feeling is prevented to improve the wearer's comfort.

In the absorbent body comprising the first sheet, the second sheet and the water absorption layer, the mass ratio of the water absorbent resin powder to a total mass of the absorbent body is preferably 60 mass % or more, more preferably 75 mass % or more, even more preferably 78 mass % or more, and most preferably 80 mass % or more, and is preferably 99 mass % or less, and more preferably 98 mass % or less. The mass ratio of the water absorbent resin powder in the absorbent body comprising the first sheet, the second sheet and the water absorption layer is calculated by the following equation.

Mass ratio(mass %)=100×mass per unit area (g/m²) of water absorbent resin powder/mass per unit area (g/m²) of absorbent body The absorbent body comprising the first sheet, the second sheet and the water absorbent resin powder can be formed to a thin type by laminating the first sheet, the water absorbent resin powder and the second sheet, followed by compressing them. For example, if a thermal bonding synthetic fiber is contained in the absorbent body, the first sheet, the water absorbent resin powder and the second sheet can be adhered together firmly by compressing them under heating.

The thickness of the absorbent body is not particularly limited, but is preferably 5 mm or less, more preferably 3 mm or less, and even more preferably 2 mm or less. Further, the mass per unit area of the absorbent body is preferably 165 g/m² or more, more preferably 200 g/m² or more, and even more preferably 300 g/m² or more, and is preferably 700 g/m² or less, more preferably 600 g/m² or less, and even more preferably 500 g/m² or less. If the mass per unit area is 165 g/m² or more, the strength of the absorbent body further improves. If the mass per unit area is 700 g/m² or less, the texture of the absorbent body becomes better.

Diffusion Layer

The diffusion layer is composed of a synthetic fiber assembly substantially having no water absorption. This diffusion layer can readily take body fluid into the synthetic fiber assembly, and diffuse the body fluid in the planar direction and the thickness direction of the diffusion layer. Further, since the diffusion layer substantially has no water absorption, almost all the body fluid taken into the diffusion layer is finally absorbed by the absorbent body. As a result, fluid remaining in the diffusion layer decreases and fluid return to the skin surface is suppressed, thus dryness after absorbing body fluid becomes better.

In the synthetic fiber assembly, the constituting fibers thereof are not adhered and tangled intentionally, i.e. the synthetic fiber assembly is different from a nonwoven fabric. Examples of the material of the synthetic fiber constituting the synthetic fiber assembly include: polyolefin such as polyethylene and polypropylene; halogenated olefin such as polytetrafluoroethylene and polyvinyl chloride; polyester such as polyethylene terephthalate (PET) and polybutylene terephthalate; polyether such as polyacetal; polyacryl such as polymethyl methacrylate and polyacrylonitrile; polyamide such as polyamide 6 (nylon 6), polyamide 12 (nylon 12) and polyamide 66 (nylon 66); polystyrene, polycarbonate; and the like.

The solubility parameter (SP value) of the material of the synthetic fiber is preferably 6.0 $(J/cm^3)^{1/2}$ or more, more preferably 7.4 $(J/cm^3)^{1/2}$ or more, even more preferably 7.6 $(J/cm^3)^{1/2}$ or more, and most preferably 7.8 $(J/cm^3)^{1/2}$ or more, and is preferably 14.5 $(J/cm^3)^{1/2}$ or less, more preferably 13.5 $(J/cm^3)^{1/2}$ or less, even more preferably 11.5 $(J/cm^3)^{1/2}$ or less, and most preferably 11.0 $(J/cm^3)^{1/2}$ or less. If the SP value is 6.0 $(J/cm^3)^{1/2}$ or more, the diffusion of body fluid becomes better, and if the SP value is 14.5 $(J/cm^3)^{1/2}$ or less, the synthetic fiber is unlikely to absorb body fluid, thus the diffusion of body fluid becomes better even in the repeated absorption. It is noted that the SP value is a value calculated according to the method proposed by Fedors et al (refer to Robert F. Fedors, "A method for estimating both the solubility parameters and molar volumes of liquids", Polymer Engineering & Science, February 1974, Volume 14, Issue 2, p. 147-154.).

The cross sectional shape of the synthetic fiber is not particularly limited, and may be a circular shape, an elliptical shape, a triangular shape, L shape, T shape, Y shape, W shape, an eight-leaf shape, a flat shape (such as a boomerang shape, a wave shape, a cocoon shape, and a cuboidal shape), a polygonal shape such as a dog bone shape, a multilobal shape, a hollow shape, or an irregular shape. From the standpoint of improving dryness after absorbing body fluid, the cross sectional shape of the synthetic fiber is preferably a circular shape or an elliptical shape.

The fineness of the synthetic fiber is preferably 1 dtex or more, more preferably 1.2 dtex or more, and even more preferably 1.5 dtex or more, and is preferably 60 dtex or less, more preferably 58 dtex or less, and even more preferably 55 dtex or less. If the fineness is 1 dtex or more, the diffusion of body fluid becomes better, and if the fineness is 60 dtex or less, the texture of the diffusion layer becomes better.

The synthetic fiber constituting the synthetic fiber assembly may be either a long fiber or a short fiber. If the long fiber is used as the synthetic fiber, the diffusion of body fluid in the diffusion layer can be further improved, and the cushioning property of the diffusion layer can also be improved. From the standpoint of improving the cushioning property of the diffusion layer, the fiber length of the long fiber is preferably more than 20 mm. On the other hand, if the short fiber is used as the synthetic fiber, forming of the planar shape of the diffusion layer becomes easy, and a complex shape can also be formed. In the case of using the short fiber, the fiber length thereof is preferably 1 mm or more, more preferably 1.5 mm or more, and even more preferably 2 mm or more, and is preferably 20 mm or less, more preferably 18 mm or less, and even more preferably 16 mm or less.

The mass per unit area of the diffusion layer is preferably 100 g/m² or more, more preferably 150 g/m² or more, and even more preferably 200 g/m² or more, and is preferably 800 g/m² or less, more preferably 600 g/m² or less, and even more preferably 500 g/m² or less. If the thickness is 100 g/m² or more, the texture of the absorbent article becomes better, and if the thickness is 800 g/m² or less, the fitness of the absorbent article becomes better.

The thickness of the diffusion layer is preferably 0.5 mm or more, more preferably 0.75 mm or more, and even more preferably 1 mm or more, and is preferably 40 mm or less, more preferably 30 mm or less, and even more preferably 20 mm or less. If the thickness of the diffusion layer is 0.5 mm or more, the diffusion of body fluid becomes better, and if the thickness is 20 mm or less, the fitness of the absorbent article becomes better.

The absorbent body may be disposed on the upper surface side (skin surface side) of the diffusion layer, or disposed on the lower surface side (external surface side) of the diffusion layer. From the standpoint of further improving dryness after absorbing body fluid, the absorbent body is preferably disposed on the upper surface side of the diffusion layer. If the absorbent body is disposed on the upper surface side of the diffusion layer, the body fluid that is not absorbed immediately, of the body fluid taken into the absorbent article, passes through the absorbent body and reaches the lower diffusion layer. The body fluid that reaches the diffusion layer is diffused in the planar direction of the diffusion layer, and absorbed from the lower surface (external surface) side of the absorbent body. That is, the body fluid is absorbed from both the upper surface and lower surface of the absorbent body, thus the absorption area increases. As a result, the absorbent article of the present invention exhibits a high absorption speed. Further, the body fluid absorbed from the lower surface side of the absorbent body does not pass through the absorbent body to return to the upper surface (skin surface) side. Thus, the absorbent article of the present invention also exhibits excellent dryness after absorbing body fluid.

The absorbent body and the diffusion layer may be formed respectively by fixing the water absorbent material, the synthetic fiber assembly or the like to a paper sheet such as tissue paper or a liquid permeable nonwoven fabric sheet, or by wrapping the water absorbent material, the synthetic fiber assembly or the like with a paper sheet such as tissue paper or a liquid permeable nonwoven fabric sheet, and molding the wrapped product into a desired shape.

The planar view shape of the absorbent body and the diffusion layer is not particularly limited, and examples thereof include a rectangular shape, an hourglass shape, a gourd shape, a battledore shape, and the like. From the standpoint of further decreasing fluid remaining in the diffusion layer, the planar view shape of the absorbent body is substantially identical to the planar view shape of the diffusion layer. In the present invention, because the water absorbent resin powder having a high liquid passing speed is used in the absorbent body, even no opening region (a region where no water absorbent resin powder is present) penetrating the thickness direction is formed in the absorbent body, the high absorption speed can be achieved. Thus, from the standpoint of dryness after absorbing body fluid, it is preferred that no opening region is formed in the absorbent body.

Figure 2:
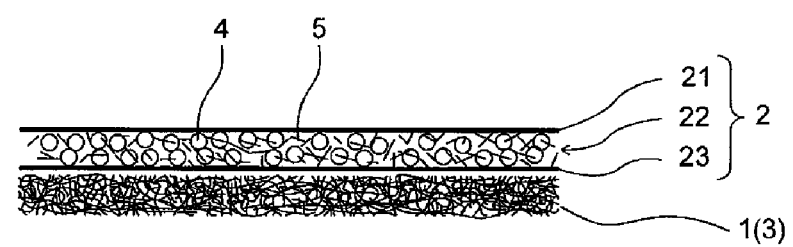
FIG. 2 is a cross sectional view along line X-X in FIG. 1.
Figure 2:
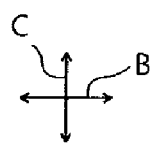

In the following, although description of a preferable embodiment of the absorbent body and the diffusion layer in the absorbent article of the present invention will be provided with reference to the drawings, the present invention is not limited to the mode that has been diagrammatically represented. FIG. 1 and FIG. 2 are schematic views showing an embodiment 1 of the absorbent body and the diffusion layer of the present invention. FIG. 1 is a schematic perspective view observed from the skin surface side, and FIG. 2 is a cross sectional view along line X-X in FIG. 1. It is noted that, in FIG. 1 and FIG. 2, with respect to C direction on the paper surface, the upper side is the skin surface side, whereas the lower side is the external surface side.

The preferable embodiment 1 combining an absorbent body and a diffusion layer includes two layers, namely, the absorbent body where the water absorbent resin powder satisfying the requirements (a) to (c), and the diffusion layer composed of the synthetic fiber assembly substantially having no water absorption; and the absorbent body is disposed on the upper surface side of the diffusion layer.

In the combination shown in FIG. 1, both the diffusion layer 1 and the absorbent body 2 have a rectangular shape with a longitudinal direction A and a short direction B, and the planar view shapes of the diffusion layer 1 and the absorbent body 2 are substantially identical.

The diffusion layer 1 is composed of a fiber assembly 3. The absorbent body 2 comprises a first sheet 21, an air-laid water absorption layer 22 and a second sheet 23. The air-laid water absorption layer 22 includes a water absorbent resin powder 4 and a short fiber 5, and is obtained by the air laying method. The air-laid water absorption layer 22 is disposed between the first sheet 21 and the second sheet 23. The planar view shapes of the diffusion layer 1 and the water absorption layer 22 of the absorbent body 2 are substantially identical.

In FIG. 1, although a rectangular shape is diagrammatically represented as the shapes of the diffusion layer 1 and the absorbent body 2, the shapes of those may be an hourglass shape, a gourd shape, a battledore shape, or the like. In addition, the planar view shape of the absorbent body 2 may be smaller or larger than the planar view shape of the diffusion layer 1. In FIG. 1, the diffusion layer 1 and the absorbent body 2, each having one layer, are diagrammatically represented. However, the diffusion layer 1 and the absorbent body 2 may have two layers or more, as long as they have at least one layer. In addition, a nonwoven fabric layer or an adhesive layer may be inserted between the diffusion layer 1 and the absorbent body 2. Furthermore, the diffusion layer 1 and the absorbent body 2 may be wrapped with a paper sheet such as tissue paper or a liquid permeable nonwoven fabric sheet and molded into a desired shape, respectively.

In FIG. 1, although the absorbent body 2 comprising the first sheet 21, the air-laid water absorption layer 22 and the second sheet 23 is diagrammatically represented, the absorbent body 2 is not limited to this configuration. For example, the absorbent body 2 may be the one where the first sheet 21 and the second sheet 23 are not disposed, and only includes the air-laid water absorption layer 22. In addition, the absorbent body 2 may be the one composed of the water absorbent resin powder 4 and the base material fiber.

Absorbent Article

Next, description of specific application examples of the absorbent article of the present invention will be provided. Examples of the absorbent article of the present invention include absorbent articles used for absorbing body fluid discharged from the human body, such as an incontinence pad, a disposable diaper, a sanitary napkin, and a breast-milk pad.

When the absorbent article is an incontinence pad or a sanitary napkin, for example, the absorbent body and the diffusion layer are disposed between the liquid permeable top sheet and the liquid impermeable back sheet. Examples of the shape of the incontinence pad or the sanitary napkin include a substantially rectangular shape, an hourglass shape, a gourd shape, and the like. In addition, a liquid impermeable side sheet may be formed on both sides of the liquid permeable top sheet in the width direction, where necessary. The side sheet is joined to the upper surface of both sides of the top sheet in the width direction, and the side sheet inward of the joining point in the width direction forms one pair of rise flaps along both side edges of the absorbent body.

The liquid permeable top sheet is a liquid permeable sheet material and is, for example, a nonwoven fabric formed from a hydrophilic fiber. The liquid permeable top sheet quickly captures the body fluid from the wearer, and transfers the body fluid to the absorbent body. The nonwoven fabric used as the top sheet is, for example, a point-bonded nonwoven fabric, an air-through nonwoven fabric, a spunlace nonwoven fabric, or a spunbond nonwoven fabric. As hydrophilic fibers forming these nonwoven fabrics, cellulose, rayon, cotton, and the like are generally used. It is noted that as the top sheet, a liquid permeable nonwoven fabric that is formed from a hydrophobic fiber (e.g., polypropylene, polyethylene, polyester, polyamide, and nylon) whose surface is hydrophilized with a surfactant may be used.

As the liquid impermeable sheet used for the back sheet and the side sheet, a water-repellent or liquid impermeable nonwoven fabric (e.g., a spunbond nonwoven fabric, a meltblown nonwoven fabric, and an SMS (spunbond-meltblown-spunbond) nonwoven fabric) formed from a hydrophobic fiber (e.g., polypropylene, polyethylene, polyester, polyamide, and nylon), or a water-repellent or liquid impermeable plastic film is used. The back sheet and the side sheet prevent the body fluid that reaches the liquid impermeable sheet, from oozing out of the absorbent article. If a plastic film is used as the liquid impermeable sheet, a moisture-permeable (air-permeable) plastic film is preferably used from the standpoint that humid feeling is prevented to improve the wearer's comfort. In addition, a paper sheet may be disposed between the plastic film and the absorbent body or the diffusion layer to provide better diffusion and shape stability.

When the absorbent article is a disposable diaper, examples of the disposable diaper include: a tape-type disposable diaper that has one pair of securing members on left and right sides of a back portion or a front abdominal portion, and that forms, because of the securing members, a pants shape when being worn; and a pants-type disposable diaper having a waist opening and one pair of leg openings formed by joining a front abdominal portion and a back portion together.

When the absorbent article is a disposable diaper, in the disposable diaper, for example, a laminated body including an inner sheet and an outer sheet may form a diaper main body including a front abdominal portion, a back portion, and a crotch portion located between these portions, and the absorbent body and the diffusion layer may be disposed on the crotch portion. Furthermore, the disposable diaper may include, for example, a laminated body having the absorbent body and the diffusion layer disposed between a top sheet and a back sheet, and the laminated body may include a front abdominal portion, a back portion, and a crotch portion located between these portions. It is noted that, with regard to the front abdominal portion, the back portion, and the crotch portion, when the disposable diaper is worn, a portion placed on the abdominal side of the wearer is referred to as a front abdominal portion, a portion placed on the hip side of the wearer is referred to as a back portion, and a portion located between the front abdominal portion and the back portion and placed on the crotch of the wearer is referred to as a crotch portion. The inner sheet is preferably hydrophilic or water-repellent, and the outer sheet is preferably water-repellent.

The absorbent article preferably has rise flaps disposed along both side-edge portions of the absorbent body. The rise flaps, for example, may be disposed on both side edge portions of the top surface of the absorbent body in the width direction, or may be disposed on both outer sides of the absorbent body in the width direction. By providing the rise flaps, side leakage of body fluid can be prevented. The rise flaps may be formed by causing inward edges of side sheets provided on both sides of the top sheet in the width direction, to rise. The rise flaps and the side sheets are preferably water-repellent.

Figure 3:
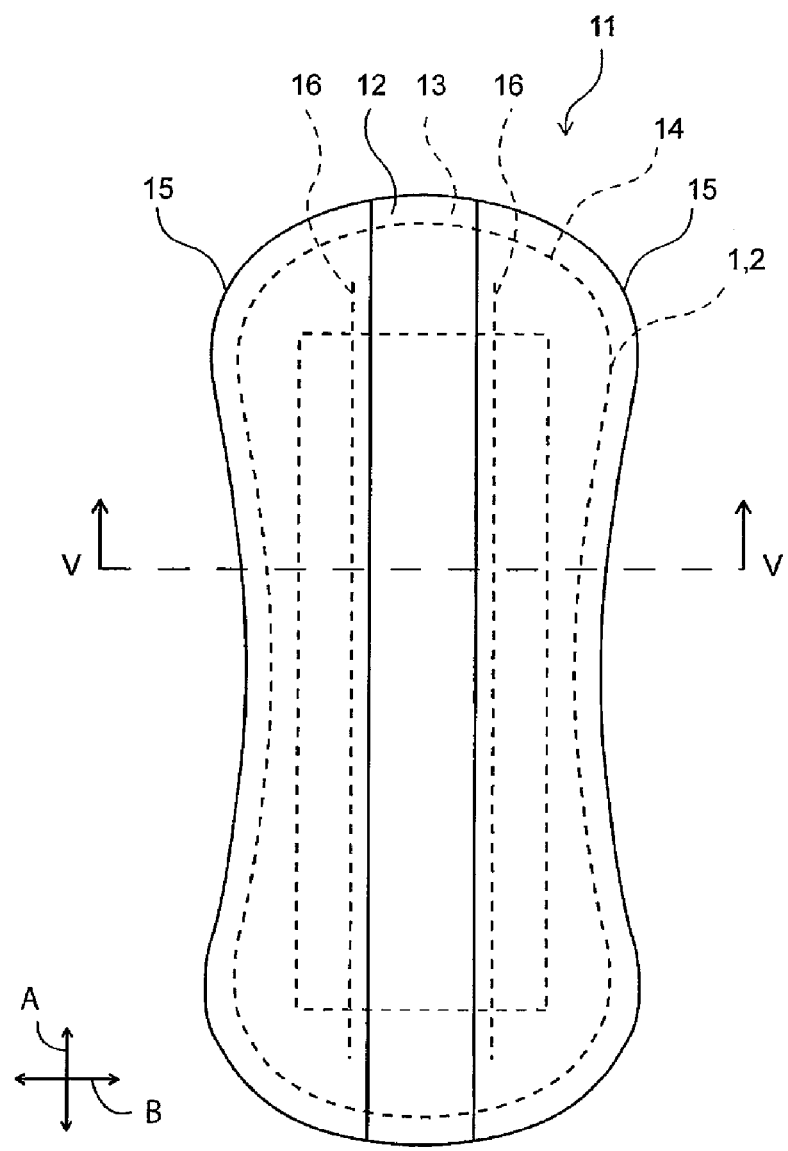
FIG. 3 is a schematic planar view of an absorbent article according to a preferable embodiment of the present invention.
Figure 4:
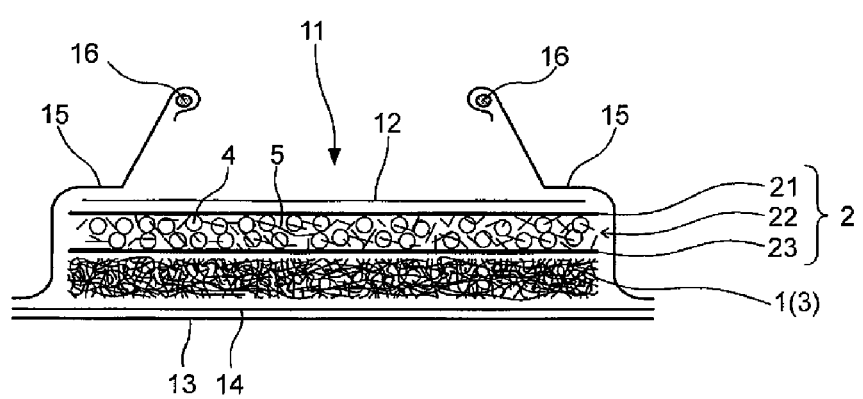
FIG. 4 is a cross sectional view along line V-V in FIG. 3.

Next, using an incontinence pad as an example, the absorbent article of the present invention will be described with reference to FIG. 3 and FIG. 4. FIG. 3 shows a planar view of an incontinence pad. FIG. 4 shows a cross sectional view along line V-V of the incontinence pad in FIG. 3. It is noted that, in the figures, arrow B is defined as the width direction and arrow A is defined as the longitudinal direction. Furthermore, a direction on the surface formed by arrows A and B is defined as a planar direction.

An incontinence pad 11 includes a liquid permeable top sheet 12, a liquid impermeable back sheet 13, and a diffusion layer 1 and an absorbent body 2 disposed between these sheets. In addition, tissue paper 14 is disposed between the liquid impermeable back sheet 13 and the diffusion layer 1. FIG. 4 shows a cross sectional view of the incontinence pad 11. In this figure, although the embodiment 1 is diagrammatically represented as the combination of the diffusion layer 1 and the absorbent body 2, the configuration of the absorbent body is not limited thereto.

The top sheet 12 is disposed so as to face the skin at the crotch portion of the wearer, and allows the body fluid from the wearer to pass through. The body fluid that has passed through the top sheet 12 is taken into the absorbent body 2, and then absorbed by an air-laid water absorption layer 22. In addition, the water absorbent resin powder 4 used in the air-laid water absorption layer 22 has a high liquid passing speed, thus a part of the body fluid taken into the absorbent body 2 diffuses to reach the lower diffusion layer 1. The body fluid that reaches the diffusion layer 1 is diffused in the planar direction of the diffusion layer 1, and then absorbed from the external surface side (lower surface side in FIG. 4) of the upper absorbent body 2. Therefore, the incontinence pad 11 can immediately absorb the body fluid since most of the water absorbent resin powder 4 included in the absorbent body 2 can effectively contribute to the absorption of the body fluid. The back sheet 13 prevents the body fluid from leaking outside.

Side sheets 15 extending in the longitudinal direction A of the incontinence pad 11 are joined on both side edges in the width direction B of the top sheet 12. The side sheets 15 are formed from a liquid impermeable plastic film, a water-repellent nonwoven fabric, or the like. The side sheets 15 have rise elastic members 16 disposed at inward edges in the width direction of the incontinence pad 11. When the incontinence pad 11 is used, the inward edges of the side sheets 15 rise toward the skin of the wearer through contractive force of the rise elastic members 16 to prevent side leakage of body fluid.

EXAMPLE

Hereinafter, the present invention will be described in detail by means of examples. However, the present invention is not limited to the following examples, changes and embodiments that do not depart from the gist of the present invention are included in the scope of the present invention.
[Evaluation Methods]
(Method for Measuring Bulk Density)

Measurement of a bulk density was conducted according to JIS K6219-2 (2005). A water absorbent resin powder that was a sample was poured into a center portion of a cylindrical container whose mass and capacity were known (a stainless steel container having a diameter of 100 mm and a capacity of 1000 ml), from a height of 50 mm or less from the upper end of the container. At that time, a sufficient amount of the sample was poured into the cylindrical container such that the poured sample formed a triangular pyramid above the upper end of the cylindrical container. Then, the excessive sample above the upper end of the cylindrical container was swept down using a spatula, and the mass of the container in this state was measured. The mass of the container itself was subtracted from the measured value to obtain the mass of the sample, and the mass of the sample was divided by the capacity of the container to calculate a bulk density which was an object. The measurement was conducted five times (n=5), the highest and lowest values were removed, and the average of the remaining three values was regarded as a measured value. It is noted that these measurements were conducted at 23 plus or minus 2 degrees centigrade and a relative humidity of 50 plus or minus 5%, and samples were stored in the same environment for 24 hours or longer prior to the measurements and then were subjected to the measurements.

(Method for Measuring Water Absorption Speed by Vortex Method)

50 mL of a saline (0.9 wt % sodium chloride solution) and a magnetic stir tip (a diameter at center portion: 8 mm, a diameter at both end portions: 7 mm, length: 30 mm, the surface was coated with a fluororesin) were placed into a 100 mL glass beaker, and the beaker was placed on a magnetic stirrer ("HPS-100" manufactured by AS ONE Corporation). The rotational speed of the magnetic stirrer was adjusted to 600 plus or minus 60 rpm, and the saline was stirred. 2.0 g of a sample was added to the solution at the center of the vortex of the saline being stirred, and the water absorption speed (seconds) of the water absorbent resin powder was measured according to JIS K 7224 (1996). Specifically, a stopwatch was started at the time when the addition of the water absorbent resin powder, which was the sample, to the beaker was completed. The stopwatch was stopped at the time when the stirrer tip was covered with the test solution (the time when the vortex disappears and the solution surface became flat), and the time (seconds) was recorded as a water absorption speed. The measurement was conducted five times (n=5), the highest and lowest values were removed, and the average of the remaining three values was regarded as a measured value. It is noted that these measurements were conducted at 23 plus or minus 2 degrees centigrade and a relative humidity of 50 plus or minus 5%, and samples were stored in the same environment for 24 hours or longer prior to the measurements and then were subjected to the measurements.

(Method for Measuring Liquid Passing Speed Under Load)

In a 100 mL glass beaker, 0.32 plus or minus 0.005 g of a water absorbent resin powder that was a sample was immersed in 100 mL of a saline (0.9 wt % sodium chloride solution) and allowed to stand for 60 minutes, thereby swelling the water absorbent resin powder. Separately, a filtration cylindrical tube was prepared in which a wire mesh (openings: 150 μm, a bio-column sintered stainless steel filter 30SUS sold by Sansyo Co., Ltd) and a narrow tube (inner diameter: 4 mm, length: 8 cm) equipped with a cock (inner diameter: 2 mm) were provided at the lower end of an opening portion of a cylinder (inner diameter 25.4 mm) that stood vertically. All the content within the beaker including the swollen measurement sample was placed into the cylindrical tube in a state where the cock was closed. Next, a cylindrical bar that had a diameter of 2 mm and had, at its end, a wire mesh having openings of 150 μm and a diameter of 25 mm was inserted into the filtration cylindrical tube such that the wire mesh came into contact with the measurement sample, and further a weight was placed such that a load of 2.0 kPa was applied to the measurement sample. In this state, the filtration cylindrical tube was allowed to stand for 1 minute. Then, the cock was opened to allow the solution to flow out, and the time ($T_1$) (seconds) taken until the solution level within the filtration cylindrical tube reached a 40 mL scale mark from a 60 mL scale mark (i.e., 20 mL of the solution passes) was measured. A liquid passing speed under a load of 2.0 kPa was calculated from the following equation using the measured time $T_1$ (seconds). It is noted that in the equation, $T_0$ (seconds) was a measured value of a time taken for 20 mL of a saline to pass through the wire mesh in a state where no measurement sample was put in the filtration cylindrical tube.

Liquid-passing speed under load (seconds)=$(T_1-T_0)$

The measurement was conducted five times (n=5), the highest and lowest values were removed, and the average of the remaining three values was regarded as a measured value. It is noted that these measurements were conducted at 23 plus or minus 2 degrees centigrade and a relative humidity of 50 plus or minus 5%, and samples were stored in the same environment for 24 hours or longer prior to the measurements and then were subjected to the measurements.

(Moisture Absorption Blocking Ratio)

10.0 g of a sample was uniformly placed into an aluminum cup having a bottom diameter of 52 mm and a height of 22 mm (a foil container, product number 107 manufactured by Toyo Aluminium Ecko Products Co., Ltd.), and the cup was kept still in a constant temperature and humidity chamber at 40 degrees centigrade and a relative humidity of 80% RH for 3 hours. Then, the sample was lightly sieved with a 12-mesh wire mesh (openings: 1.4 mm), the weight of powdered matter of the measurement sample that had caused blocking due to moisture absorption and had not passed through the 12 mesh and the mass of the sample that had passed through the 12 mesh were measured, and a moisture absorption blocking ratio which was an object was calculated according to the following equation.

Moisture absorption blocking ratio (%)=(mass of sample not passing through 12 mesh after being kept still)/(mass of sample not passing through 12 mesh after being kept still+mass of sample passing through 12 mesh after being kept still)×100

The measurement was conducted five times (n=5), the highest and lowest values were removed, and the average of the remaining three values was regarded as a measured value. It is noted that these measurements were conducted at 23 plus or minus 2 degrees centigrade and a relative humidity of 50 plus or minus 5%, and samples were stored in the same environment for 24 hours or longer prior to the measurements and then were subjected to the measurements.

(Method for Measuring Absorption Ratio)

Measurement of an absorption ratio was conducted according to JIS K 7223 (1996). A nylon mesh having openings of 63 μm (JIS Z8801-1: 2000) was cut into a rectangle having a width of 10 cm and a length of 40 cm and folded in half at a center in its longitudinal direction, and both ends thereof were heat sealed, to produce a nylon bag having a width of 10 cm (inside dimension: 9 cm) and a length of 20 cm. 1.00 g of a measurement sample was precisely weighted and placed into the produced nylon bag such that the sample was uniform at the bottom of the nylon bag. The nylon bag containing the sample was immersed in a saline. After 60 minutes from start of the immersion, the nylon bag was taken out from the saline, and was hung vertically for 1 hour to drain the nylon bag. Then, the mass ($F_1$) of the sample was measured. In addition, the same operation was conducted without using any sample, and a mass $F_0$ (g) at that time was measured. Then, an absorption ratio which was an object was calculated according to the following equation from these masses $F_1$ and $F_0$ and the mass of the sample.

Absorption ratio (g/g)=($F_1$-$F_0$)/mass of sample (Method for Measuring Water Retaining Capacity)

Measurement of a water retaining capacity was conducted according to JIS K 7223 (1996). A nylon mesh having openings of 63 μm (JIS Z8801-1: 2000) was cut into a rectangle having a width of 10 cm and a length of 40 cm and folded in half at a center in its longitudinal direction, and both ends thereof were heat sealed, to produce a nylon bag having a width of 10 cm (inside dimension: 9 cm) and a length of 20 cm. 1.00 g of a measurement sample was precisely weighted and placed into the produced nylon bag such that the sample was uniform at the bottom of the nylon bag. The nylon bag containing the sample was immersed in a saline. After 60 minutes from start of the immersion, the nylon bag was taken out from the saline, and was hung vertically for 1 hour to drain the nylon bag. Then, the nylon bag was dehydrated using a centrifugal hydroextractor (model H-130C special type manufactured by Kokusan Co., Ltd.). The dehydrating conditions were 143 G (800 rpm) and 2 minutes. A mass ($R_1$) after the dehydration was measured. In addition, the same operation was conducted without using any sample, and a mass $R_0$ (g) at that time was measured. Then, a water retaining capacity which was an object was calculated according to the following equation from these masses $R_1$ and $R_0$ and the mass of the sample.

Water retaining capacity (g/g)=($R_1$-$R_0$-mass of sample)/mass of sample

[Synthesis of Water Absorbent Resin Powder]

Synthesis Example 1

155 parts by mass (2.15 parts by mol) of a water-soluble ethylenically unsaturated monomer (a1-1) {acrylic acid manufactured by Mitsubishi Chemical Corporation, purity: 100%}, 0.6225 parts by mass (0.0024 parts by mol) of an internal crosslinking agent (b1) {pentaerythritol triallyl ether manufactured by Daiso Co., Ltd.}, and 340.27 parts by mass of deionized water were kept at 1 degree centigrade while being stirred and mixed. After nitrogen was introduced into the mixture to reduce a dissolved oxygen amount to 0.1 ppm or less, 0.31 parts by mass of a 1 mass % aqueous hydrogen peroxide solution, 1.1625 parts by mass of a 1 mass % aqueous ascorbic acid solution, and 2.325 parts by mass of a 0.5 mass % aqueous 2,2'-azobis[2-methyl-N-(2-hydroxyethyl)-propionamide]solution were added and mixed to initiate polymerization. After the temperature of the mixture reached 85 degrees centigrade, the polymerization was conducted at 85 plus or minus 2 degrees centigrade for about 10 hours, to obtain a water-containing gel (1).

Next, while 502.27 parts by mass of the water-containing gel (1) was chopped with a mincing machine ("12VR-400K" manufactured by KIRE ROYAL Co., LTD), 128.42 parts by mass of a 48.5 mass % aqueous sodium hydroxide solution was added and mixed, and further 3 parts by mass of a 1 mass % aqueous ethylene glycol glycidyl ether solution was added and mixed, to obtain a chopped gel (2). Further, the chopped gel (2) was dried with an air-flow band dryer (200 degrees centigrade, wind velocity: 5 m/second) to obtain a dried product. The dried product was pulverized with a juicer mixer ("OSTERIZER BLENDER" manufactured by Oster Co.), and then the particle size thereof was adjusted to 150 μm to 710 μm using sieves having openings of 150 μm and 710 μm, to obtain a dried product particle.

While 100 parts by mass of the dried product particle was stirred at a high speed (with a high speed stirring turbulizer manufactured by Hosokawa Micron Corporation, rotational speed: 2000 rpm), 5 parts by mass of a 2 mass % water/methanol mixed solution (weight ratio of water/methanol=70/30) of ethylene glycol diglycidyl ether was added by spraying and mixed, and the mixture was kept still at 150 degrees centigrade for 30 minutes to achieve surface crosslinking, thereby obtaining a crosslinked polymer (A). With respect to 100 parts by mass of the crosslinked polymer (A), 0.5 part by mass of silica ("Aerosil 380" manufactured by Toshin Chemicals Co., Ltd.) and 0.02 part by mass of a carboxy-modified polysiloxane ("X-22-3701 E" manufactured by Shin-Etsu Chemical Co., Ltd.) were added as a surface modifier (B), followed by stirring at 85 degrees centigrade for 60 minutes. The weight average particle size of the obtained resin powder was adjusted to 400 μm to obtain a water absorbent resin powder 1.

Synthesis Example 2

A water absorbent resin powder 2 was obtained in the same manner as in the synthetic example 1, except that "the chopped gel (2) was dried with an air-flow band dryer (200 degrees centigrade, wind velocity: 5 m/second)" was changed to "the chopped gel (2) was dried with an air-flow band dryer (150 degrees centigrade, wind velocity: 5 m/second)".

Synthesis Example 3

A water absorbent resin powder 3 was obtained in the same manner as in the synthetic example 1, except that "the chopped gel (2) was dried with an air-flow band dryer {200 degrees centigrade, wind velocity: 5 m/second}" was changed to "the chopped gel (2) was dried with an air-flow band dryer {150 degrees centigrade, wind velocity: 2 m/second}".

Synthesis Example 4

A water absorbent resin powder 4 was obtained in the same manner as in the synthetic example 3, except that "the weight average particle size of the obtained resin powder was adjusted to 400 μm" was changed to "the weight average particle size of the obtained resin powder was adjusted to 530 μm".

Synthesis Example 5

A water absorbent resin powder 5 was obtained in the same manner as in the synthetic example 2, except that "the weight average particle size of the obtained resin powder was adjusted to 400 μm" was changed to "the weight average particle size of the obtained resin powder was adjusted to 320 μm".

Synthesis Example 6

A water absorbent resin powder 6 was obtained in the same manner as in the synthetic example 1, except that "the weight average particle size of the obtained resin powder was adjusted to 400 μm" was changed to "the weight average particle size of the obtained resin powder was adjusted to 280 μm".

Synthetic Example 7

A water absorbent resin powder 7 was obtained in the same manner as in the synthetic example 2, except that "0.5 part by mass of silica ("Aerosil 380" manufactured by Toshin Chemicals Co., Ltd.) and 0.02 part by mass of a carboxy-modified polysiloxane ("X-22-3701 E" manufactured by Shin-Etsu Chemical Co., Ltd.) were used as a surface modifier (B)" was changed to "0.5 part by mass of silica ("Aerosil 380" manufactured by Toshin Chemicals Co., Ltd.) was used as a surface modifier (B)".

Synthetic Example 8

A water absorbent resin powder 8 was obtained in the same manner as in the synthetic example 2, except that "0.5 part by mass of silica ("Aerosil 380" manufactured by Toshin Chemicals Co., Ltd.) and 0.02 part by mass of a carboxy-modified polysiloxane ("X-22-3701E" manufactured by Shin-Etsu Chemical Co., Ltd.) were used as a surface modifier (B)" was changed to "0.5 part by mass of silica ("Aerosil 200" manufactured by Toshin Chemicals Co., Ltd.) was used as a surface modifier (B)".

Synthetic Example 9

A water absorbent resin powder 9 was obtained in the same manner as in the synthetic example 2, except that "0.5 part by mass of silica ("Aerosil 380" manufactured by Toshin Chemicals Co., Ltd.) and 0.02 part by mass of a carboxy-modified polysiloxane ("X-22-3701E" manufactured by Shin-Etsu Chemical Co., Ltd.) were used as a surface modifier (B)" was changed to "0.02 part by mass of a carboxy-modified polysiloxane ("X-22-3701E" manufactured by Shin-Etsu Chemical Co., Ltd.) was used as a surface modifier (B)".

Synthetic Example 10

A water absorbent resin powder 10 was obtained in the same manner as in the synthetic example 2, except that "0.5 part by mass of silica ("Aerosil 380" manufactured by Toshin Chemicals Co., Ltd.) and 0.02 part by mass of a carboxy-modified polysiloxane ("X-22-3701E" manufactured by Shin-Etsu Chemical Co., Ltd.) were used as a surface modifier (B)" was changed to "0.02 part by mass of an amino-modified polysiloxane ("KF-880" manufactured by Shin-Etsu Chemical Co., Ltd.) was used as a surface modifier (B)".

Comparative Synthetic Example 1

A comparative water absorbent resin powder 1 was obtained in the same manner as in the synthetic example 1, except that "the weight average particle size of the obtained resin powder was adjusted to 400 μm" was changed to "the weight average particle size of the obtained resin powder was adjusted to 600 μm".

Comparative Synthetic Example 2

A comparative water absorbent resin powder 2 was obtained in the same manner as in the synthetic example 2, except that "the weight average particle size of the obtained resin powder was adjusted to 400 μm" was changed to "the weight average particle size of the obtained resin powder was adjusted to 280 μm".

Comparative Synthetic Example 3

2 parts of a polyethylene glycol ("PEG 200" manufactured by Sanyo Chemical Industries, Ltd.) was added to 100 parts by weight of the water absorbent resin powder 7, followed by stirring at 85 degrees centigrade for 60 minutes. The weight average particle size of the obtained resin powder was adjusted to 400 μm to obtain a comparative water absorbent resin powder 3.

Comparative Synthetic Example 4

A commercially available product ("AQUA KEEP SA60SXII" manufactured by Sumitomo Seika Chemicals Co., Ltd.) was used as a comparative water absorbent resin powder 4.

With regard to the water absorbent resin powders obtained in the synthetic examples 1 to 10 and the comparative synthetic examples 1 to 4, the measured physical properties are shown in Table 1.

TABLE 1

| | Physical properties of water absorbent resin powder | | | | | | |
|---|---|---|---|---|---|---|---|
| | Bulk density (g/ml) | Absorption speed (seconds) | Liquid passing speed under load (seconds) | Moisture absorption blocking ratio (%) | Absorption ratio (g/g) | Water retaining capacity (g/g) | Weight average particle size (μm) |
| Water absorbent resin powder 1 | 0.45 | 24 | 7 | 1 | 44 | 26 | 400 |
| Water absorbent resin powder 2 | 0.55 | 30 | 5 | 1 | 46 | 28 | 400 |
| Water absorbent resin powder 3 | 0.62 | 40 | 4 | 1 | 48 | 30 | 400 |
| Water absorbent resin powder 4 | 0.62 | 49 | 2 | 1 | 48 | 30 | 530 |

TABLE 1-continued

| | Physical properties of water absorbent resin powder | | | | | | |
|---|---|---|---|---|---|---|---|
| | Bulk density (g/ml) | Absorption speed (seconds) | Liquid passing speed under load (seconds) | Moisture absorption blocking ratio (%) | Absorption ratio (g/g) | Water retaining capacity (g/g) | Weight average particle size (μm) |
| Water absorbent resin powder 5 | 0.55 | 25 | 10 | 1 | 42 | 24 | 320 |
| Water absorbent resin powder 6 | 0.45 | 21 | 9 | 1 | 42 | 24 | 280 |
| Water absorbent resin powder 7 | 0.55 | 28 | 6 | 1 | 46 | 28 | 400 |
| Water absorbent resin powder 8 | 0.55 | 27 | 7 | 1 | 48 | 28 | 400 |
| Water absorbent resin powder 9 | 0.55 | 35 | 5 | 1 | 43 | 28 | 400 |
| Water absorbent resin powder 10 | 0.55 | 35 | 5 | 1 | 43 | 28 | 400 |
| Comparative water absorbent resin powder 1 | 0.62 | 52 | 2 | 1 | 49 | 31 | 600 |
| Comparative water absorbent resin powder 2 | 0.55 | 18 | 13 | 1 | 46 | 28 | 280 |
| Comparative water absorbent resin powder 3 | 0.55 | 40 | 3 | 7 | 46 | 28 | 400 |
| Comparative water absorbent resin powder 4 | 0.67 | 55 | 800 | 9 | 60 | 40 | 350 |

[Production of Absorbent Body]

<Absorbent Body 1>

As the first sheet, an air-through nonwoven fabric ("LD18" manufactured by KINSEI SEISHI Co., Ltd., mass per unit area: 18 g/m²) was used. A short fiber obtained by opening a polyester raw fiber (sheath-core structure (core: polyethylene terephthalate, sheath: polyethylene)) was accumulated on the first sheet by the air laying method to form the first web layer. The water absorbent resin powder 1 was applied to the obtained first web layer. A short fiber obtained by opening a polyester raw fiber (sheath-core structure (core: polyethylene terephthalate, sheath: polyethylene)) was accumulated on the water absorbent resin powder 1 by the air laying method to form the second web layer. An air-through nonwoven fabric ("LD18" manufactured by KINSEI SEISHI Co., Ltd., mass per unit area: 18 g/m²) which was used as the second sheet was laminated on the second web layer to obtain a laminated body. The obtained laminated body was treated with a pressure roll having a surface temperature of 150 degrees centigrade to obtain an absorbent body No. 1.

<Absorbent Bodies 2 to 10 and Comparative Absorbent Bodies 1 to 4>

Absorbent bodies No. 2 to No. 10 and comparative absorbent bodies No. 1 to No. 4 were obtained in the same manner as that of the absorbent body No. 1, except that "water absorbent resin powder 1" was changed to "water absorbent resin powders 2 to 10" or "comparative water absorbent resin powders 1 to 4".

<Absorbent Bodies 11 to 14>

Absorbent bodies 11 to 14 were obtained in the same manner as that of the absorbent body No. 2, except that the mass per unit area of SAP or the mass per unit area of raw fiber was changed.

<Absorbent Body 15>

As the first sheet, an air-through nonwoven fabric ("LD18" manufactured by Kinsei Seishi Co., Ltd., mass per unit area: 18 g/m²) was used. A short fiber obtained by opening a polyester raw fiber (sheath-core structure (core: polyethylene terephthalate, sheath: polyethylene)) and a water absorbent resin powder 2 were mixed, and the obtained mixture was accumulated on the first sheet by the air laying method to form a web layer. An air-through nonwoven fabric ("LD18" manufactured by KINSEI SEISHI Co., Ltd., mass per unit area: 18 g/m²) which was used as the second sheet was laminated on the obtained web layer to obtain a laminated body. The obtained laminated body was treated with a pressure roll having a surface temperature of 150 degrees centigrade to obtain an absorbent body No. 15.

<Comparative Absorbent Body 5>

A comparative absorbent body 5 was obtained in the same manner as that of the absorbent body No. 15, except that "water absorbent resin powder 2" was changed to "comparative water absorbent resin powder 1".

<Absorbent Body 16>

After a synthetic rubber hotmelt adhesive (mass per unit area: 10 g/m²) was applied to a spunlace nonwoven fabric (mass per unit area: 35 g/m²) which was used as the first sheet, the water absorbent resin powder 2 was applied thereon. An air-through nonwoven fabric (mass per unit area: 18 g/m²) which was used as the second sheet was laminated on the water absorbent resin powder 2 to obtain a laminated body. The obtained laminated body was thermally compressed at 170 degrees centigrade to obtain an absorbent body No. 16.

<Comparative Absorbent Body 6>

A comparative absorbent body 6 was obtained in the same manner as that of the absorbent body No. 15, except that "water absorbent resin powder 2" was changed to "comparative water absorbent resin powder 1".

Regarding each of the absorbent bodies, the mass per unit area of the water absorbent resin powder (SAP), the mass per unit area of the raw fiber, the SAP content in the air-laid water absorption layer, and the SAP content in the absorbent body are shown in Table 2.

TABLE 2

| | Type of water absorbent resin powder (SAP) | Mass per unit area of SAP [g/m²] | Mass per unit area of short fiber [g/m²] | SAP content in air-laid water absorption layer [%] | SAP content in absorbent body [%] |
|---|---|---|---|---|---|
| Absorbent body 1 | Water absorbent resin powder 1 | 400 | 30 | 93.0 | 85.8 |
| Absorbent body 2 | Water absorbent resin powder 2 | 400 | 30 | 93.0 | 85.8 |
| Absorbent body 3 | Water absorbent resin powder 3 | 400 | 30 | 93.0 | 85.8 |
| Absorbent body 4 | Water absorbent resin powder 4 | 400 | 30 | 93.0 | 85.8 |
| Absorbent body 5 | Water absorbent resin powder 5 | 400 | 30 | 93.0 | 85.8 |
| Absorbent body 6 | Water absorbent resin powder 6 | 400 | 30 | 93.0 | 85.8 |
| Absorbent body 7 | Water absorbent resin powder 7 | 400 | 30 | 93.0 | 85.8 |
| Absorbent body 8 | Water absorbent resin powder 8 | 400 | 30 | 93.0 | 85.8 |
| Absorbent body 9 | Water absorbent resin powder 9 | 400 | 30 | 93.0 | 85.8 |
| Absorbent body 10 | Water absorbent resin powder 10 | 400 | 30 | 93.0 | 85.8 |
| Absorbent body 11 | Water absorbent resin powder 2 | 400 | 215 | 65.0 | 61.4 |
| Absorbent body 12 | Water absorbent resin powder 2 | 400 | 20 | 95.2 | 87.7 |
| Absorbent body 13 | Water absorbent resin powder 2 | 200 | 30 | 87.0 | 75.2 |
| Absorbent body 14 | Water absorbent resin powder 2 | 500 | 30 | 94.3 | 88.3 |
| Absorbent body 15 | Water absorbent resin powder 2 | 400 | 30 | 93.0 | 85.8 |
| Absorbent body 16 | Water absorbent resin powder 2 | 180 | — | — | 74.1 |
| Comparative absorbent body 1 | Comparative water absorbent resin powder 1 | 400 | 30 | 93.0 | 85.8 |
| Comparative absorbent body 2 | Comparative water absorbent resin powder 2 | 400 | 30 | 93.0 | 85.8 |
| Comparative absorbent body 3 | Comparative water absorbent resin powder 3 | 400 | 30 | 93.0 | 85.8 |
| Comparative absorbent body 4 | Comparative water absorbent resin powder 4 | 400 | 30 | 93.0 | 85.8 |
| Comparative absorbent body 5 | Comparative water absorbent resin powder 1 | 400 | 30 | 93.0 | 85.8 |
| Comparative absorbent body 6 | Comparative water absorbent resin powder 1 | 180 | — | — | 74.1 |

[Production of Absorbent Article]

Example 1

An air-through nonwoven fabric ("LD18" manufactured by KINSEI SEISHI Co., Ltd., mass per unit area: 18 g/m²) which was used as a liquid permeable top sheet, the absorbent body No. 1 wrapped with tissue paper, the diffusion layer wrapped with tissue paper, and a liquid impermeable back sheet (polyethylene sheet, mass per unit area: 25 g/m²) were laminated in order from the top to produce an absorbent article 1. The planar view shape of the absorbent body No. 1 was a rectangle (15 cm×7 cm). A polypropylene raw fiber (fiber cross sectional shape: circular shape, SP value: 7.9 $(J/cm^3)^{1/2}$) was used in the diffusion layer. This diffusion layer was composed of a polypropylene fiber assembly, and substantially had no water absorption. The planar view shape of the diffusion layer was a rectangle (15 cm×7 cm), the thickness of the diffusion layer was 2 mm, and the mass per unit area of the fiber assembly was 250 g/m².

Examples 2 to 16 and Comparative Examples 1 to 6

Absorbent articles 2 to 16 and comparative absorbent articles 1 to 6 were obtained in the same manner as that in the example 1, except that "absorbent body No. 1" was changed to "absorbent bodies No. 2 to No. 16" and "comparative absorbent bodies No. 1 to 6."

<Surface Dryness Value Measured by SDME Method>

An absorbent article was immersed in artificial urine (0.03 wt % of potassium chloride, 0.08 wt % of magnesium sulfate, 0.8 wt % of sodium chloride, and 99.09 wt % of deionized water) and allowed to stand for 60 minutes, to prepare a sufficiently wet absorbent article. In addition, an absorbent article was dried by heating at 80 degrees centigrade for 2 hours, to prepare a sufficiently dried absorbent article. A detector of an SDME (Surface Dryness Measurement Equipment) tester (manufactured by WK system Co.) was placed on the sufficiently wet absorbent article to set a 100% dryness value. Next, the detector of the SDME tester was placed on the sufficiently dried absorbent article to set a 0% dryness value, thereby calibrating the SDME tester. Next, a metal ring (inner diameter: 50 mm, length: 50 mm) was set on the center of an absorbent article to be measured, and 20 ml of the artificial urine was poured thereinto. After the absorbent article was allowed to stand for 30 minutes, 20 ml of the artificial urine was poured thereinto for the second time. The time taken until the second time artificial urine was completely absorbed was measured to obtain an absorption speed. Immediately after the completion of the absorption, the metal ring was removed. The SDME detector was placed on the absorbent article, and measurement of surface dryness value was started. The values obtained after 2 minutes and 4 minutes from the start of the measurement were recorded. It is noted that the measurement was conducted, where the artificial urine, the measuring atmosphere, and the standing atmosphere were at 25 plus or minus 5 degrees centigrade and 65 plus or minus 10% RH. The results are shown in Table 3.

Because the water absorbent resin powder included in the absorbent articles 3 and 4 of the comparative examples 3 and 4 has a high moisture absorption blocking ratio, the dryness of the absorbent article is unlikely to be improved. Accordingly, it is inferred that the result of the dryness is inferior.

TABLE 3

| | | Absorbent body | | | | Absorbent article evaluation | | |
|---|---|---|---|---|---|---|---|---|
| | | Water absorbent resin powder (SAP) | | | | Second time | | |
| | Type | Type | Absorption speed (seconds) | Liquid passing speed under load (seconds) | Moisture absorption blocking ratio (%) | Absorption speed (seconds) | Surface dryness value [%] | |
| | | | | | | | after 2 minutes | after 4 minutes |
| Example 1 | Absorbent body 1 | Water absorbent resin powder 1 | 24 | 7 | 1 | 18 | 17 | 14 |
| Example 2 | Absorbent body 2 | Water absorbent resin powder 2 | 30 | 5 | 1 | 15 | 18 | 14 |
| Example 3 | Absorbent body 3 | Water absorbent resin powder 3 | 40 | 4 | 1 | 12 | 18 | 14 |
| Example 4 | Absorbent body 4 | Water absorbent resin powder 4 | 49 | 2 | 1 | 11 | 19 | 15 |
| Example 5 | Absorbent body 5 | Water absorbent resin powder 5 | 25 | 10 | 1 | 19 | 19 | 17 |
| Example 6 | Absorbent body 8 | Water absorbent resin powder 6 | 21 | 9 | 1 | 18 | 20 | 16 |
| Example 7 | Absorbent body 7 | Water absorbent resin powder 7 | 28 | 6 | 1 | 16 | 15 | 12 |
| Example 8 | Absorbent body 8 | Water absorbent resin powder 8 | 27 | 7 | 1 | 18 | 22 | 17 |
| Example 9 | Absorbent body 9 | Water absorbent resin powder 9 | 35 | 5 | 1 | 14 | 23 | 17 |
| Example 10 | Absorbent body 10 | Water absorbent resin powder 10 | 35 | 5 | 1 | 14 | 24 | 15 |
| Example 11 | Absorbent body 11 | Water absorbent resin powder 2 | 30 | 5 | 1 | 10 | 24 | 20 |
| Example 12 | Absorbent body 12 | | | | | 16 | 18 | 13 |
| Example 13 | Absorbent body 13 | | | | | 15 | 20 | 20 |
| Example 14 | Absorbent body 14 | | | | | 16 | 13 | 10 |
| Example 15 | Absorbent body 15 | | | | | 12 | 15 | 12 |
| Example 16 | Absorbent body 16 | | | | | 21 | 12 | 10 |
| Comparative example 1 | Comparative absorbent body 1 | Comparative water absorbent resin powder 1 | 52 | 2 | 1 | 51 | 44 | 33 |
| Comparative example 2 | Comparative absorbent body 2 | Comparative water absorbent resin powder 2 | 18 | 13 | 1 | 58 | 62 | 40 |
| Comparative example 3 | Comparative absorbent body 3 | Comparative water absorbent resin powder 3 | 40 | 3 | 7 | 18 | 51 | 32 |
| Comparative example 4 | Comparative absorbent body 4 | Comparative water absorbent resin powder 4 | 55 | 600 | 9 | 15 | 30 | 30 |
| Comparative example 5 | Comparative absorbent body 5 | Comparative water absorbent resin powder 1 | 52 | 2 | 1 | 52 | 22 | 20 |
| Comparative example 6 | Comparative absorbent body 6 | | | | | 63 | 73 | 51 |

As apparent from Table 3, the absorbent articles of the present invention (Examples 1 to 16) exhibit an excellent absorption speed and dryness value, compared with the absorbent articles (Comparative examples 1 to 6) which are outside the scope of the present invention. It is thought that this is because the absorbent articles of the present invention contain the water absorbent resin powder having specific physical properties, and thus the permeability and the absorbability of the absorbent articles are improved.

On the other hand, the absorbent articles (Comparative examples 1 to 6) which are outside the scope of the present invention exhibit inferior results, compared with the absorbent articles of the present invention. Because the water absorbent resin powder included in the comparative absorbent bodies 1, 5 and 6 of the comparative examples 1, 5 and 6 has a slow absorption speed, the permeability and dryness of the absorbent articles are unlikely to be improved. Accordingly, it is inferred that the results of the absorption speed and dryness are inferior. Because the water absorbent resin powder included in the absorbent article 2 of the comparative example 2 has a slow absorption speed under load, the permeability and dryness of the absorbent article are unlikely to be improved. Accordingly, it is inferred that the results of the absorption speed and dryness are inferior.

Examples 17 to 28 and Comparative Example 7

Absorbent articles 17 to 28 and a comparative absorbent article 7 were obtained in the same manner as that in the example 2, except that the fiber of the diffusion layer was changed to the fiber shown in Table 4. The diffusion layers of the absorbent articles 17 to 28 were composed of a synthetic fiber assembly, and substantially had no water absorption. The diffusion layer of the comparative absorbent article 7 was composed of a rayon fiber (regenerated plant fiber), and had water absorption.

<Surface Dryness Value Measured by SDME Method>

An absorbent article was immersed in artificial urine (0.03 wt % of potassium chloride, 0.08 wt % of magnesium sulfate, 0.8 wt % of sodium chloride, and 99.09 wt % of deionized water) and allowed to stand for 60 minutes, to prepare a sufficiently wet absorbent article. In addition, an absorbent article was dried by heating at 80 degrees centigrade for 2 hours, to prepare a sufficiently dried absorbent article. A detector of an SDME (Surface Dryness Measurement Equipment) tester (manufactured by WK system Co.) was placed on the sufficiently wet absorbent article to set a 100% dryness value. Next, the detector of the SDME tester was placed on the sufficiently dried absorbent article to set a 0% dryness value, thereby calibrating the SDME tester. Next, a metal ring (inner diameter: 50 mm, length: 50 mm)

was set on the center of an absorbent article to be measured, and 20 ml of the artificial urine was poured thereinto. After the absorbent article was allowed to stand for 30 minutes, 20 ml of the artificial urine was poured thereinto for the second time. The time taken until the second time artificial urine was completely absorbed was measured to obtain an absorption speed. Immediately after the completion of the absorption, the metal ring was removed. The SDME detector was placed on the absorbent article, and measurement of surface dryness value was started. The values obtained after 2 minutes and 4 minutes from the start of the measurement were recorded. After the absorbent article was further allowed to stand for 30 minutes, 20 ml of the artificial urine was poured thereinto for the third time. The time taken until the third time artificial urine was completely absorbed was measured to obtain an absorption speed. Immediately after the completion of the absorption, the metal ring was removed. The SDME detector was placed on the absorbent article, and measurement of surface dryness value was started. The values obtained after 2 minutes and 4 minutes from the start of the measurement were recorded. It is noted that the measurement was conducted, where the artificial urine, the measuring atmosphere, and the standing atmosphere were at 25 plus or minus 5 degrees centigrade and 65 plus or minus 10% RH. The results are shown in Table 4.

REFERENCE SIGNS LIST

1: diffusion layer, 2: absorbent body, 3: synthetic fiber assembly, 4: water absorbent resin powder, 5: short fiber, 11: incontinence pad (absorbent article), 12: top sheet, 13: back sheet, 14: tissue paper, 15: side sheet, 16: rise elastic member, 21: the first sheet, 22: air-laid water absorption layer, 23: the second sheet

The invention claimed is:
1. An absorbent article comprising:
   an absorbent body comprising a water absorbent resin powder meeting the following requirements (a) to (c),
   (a) an absorption speed measured by a vortex method: 20 seconds to 50 seconds,
   (b) a liquid passing speed under load: 10 seconds or less,
   (c) a moisture absorption blocking ratio: 5% or less; and
   a diffusion layer composed of a synthetic fiber assembly substantially having no water absorption,
   wherein a material of a synthetic fiber constituting the synthetic fiber assembly has a solubility parameter ranging from 6.0 $(J/cm^3)^{1/2}$ to 14.5 $(J/cm^3)^{1/2}$.
2. The absorbent article according to claim 1, wherein the material of the synthetic fiber constituting the synthetic fiber assembly has the solubility parameter ranging from 6.0 $(J/cm^3)^{1/2}$ to 13.5 $(J/cm^3)^{1/2}$.

TABLE 4

| | Diffusion layer | | | Absorbent article evaluation | | | | |
| | Raw fiber | | Second time | | | Third time | | |
| | Type | SP value $[(J/cm^3)^{1/2}]$ | Mass per unit area $[g/m^2]$ | Absorption speed (seconds) | Surface dryness value [%] after 2 minutes | after 4 minutes | Absorption speed (seconds) | Surface dryness value [%] after 2 minutes | after 4 minutes |
|---|---|---|---|---|---|---|---|---|---|
| Example 2 | Polypropylene | 7.9 | 250 | 15 | 18 | 14 | 21 | 28 | 23 |
| Example 17 | Polytetrafluoroethylene | 6.2 | 250 | 25 | 17 | 15 | 33 | 40 | 39 |
| Example 18 | Polyethylene | 8.0 | 250 | 15 | 18 | 15 | 22 | 28 | 21 |
| Example 19 | Polystyrene | 9.1 | 250 | 16 | 16 | 13 | 23 | 27 | 25 |
| Example 20 | Polymethylmethacrylate | 9.2 | 250 | 17 | 18 | 14 | 24 | 26 | 23 |
| Example 21 | Polyamide (nylon 12) | 9.5 | 250 | 17 | 17 | 15 | 22 | 28 | 25 |
| Example 22 | Polyvinyl choride | 9.6 | 250 | 17 | 16 | 14 | 21 | 25 | 25 |
| Example 23 | Polycarbonate | 9.8 | 250 | 18 | 18 | 13 | 20 | 27 | 25 |
| Example 24 | Polyethylene terephthalate | 10.7 | 250 | 18 | 17 | 16 | 22 | 26 | 26 |
| Example 25 | Polyacetal | 11.2 | 250 | 19 | 17 | 17 | 31 | 35 | 31 |
| Example 26 | Polyamide (nylon 6) | 12.7 | 250 | 20 | 18 | 16 | 30 | 35 | 35 |
| Example 27 | Polyamide (nylon 66) | 13.6 | 250 | 22 | 18 | 16 | 36 | 42 | 42 |
| Example 28 | Polyacrylonitrile | 14.3 | 250 | 25 | 19 | 17 | 35 | 46 | 46 |
| Comparative example 7 | Rayon | 14.8 | 250 | 25 | 35 | 30 | 45 | 59 | 55 |

As apparent from Table 4, the absorbent articles of the present invention (Examples 2, 17 to 28) exhibit an excellent absorption speed and dryness value. On the other hand, with regard to the comparative example 7 in which rayon was used in the diffusion layer, even though the absorption speed for the second time is high, the dryness is inferior because rayon has water absorption. In addition, the results of the absorption speed for the third time and the dryness are also inferior.

INDUSTRIAL APPLICABILITY

For example, the absorbent article of the present invention is useful as an absorbent article used for absorbing the body fluid excreted from the human body, and is particularly useful as an absorbent article such as an incontinence pad, a disposable diaper, a sanitary napkin, and a breast milk pad.

3. The absorbent article according to claim 1, wherein the water absorbent resin powder has a bulk density ranging from 0.45 g/ml to 0.70 g/ml.
4. The absorbent article according to claim 1, wherein the water absorbent resin powder has an absorption ratio ranging from 40 g/g to 55 g/g.
5. The absorbent article according to claim 1, wherein the water absorbent resin powder has a water retaining capacity ranging from 20 g/g to 45 g/g.
6. The absorbent article according to claim 1, wherein the water absorbent resin powder is obtained by treating, with a surface modifier (B), a crosslinked polymer (A) obtained by polymerizing a monomer composition containing: a water-soluble ethylenically unsaturated monomer (a1) and/or a hydrolyzable monomer (a2) producing the water-soluble ethylenically unsaturated monomer (a1) by hydrolysis; and an internal crosslinking agent (b).

7. The absorbent article according to claim 6, wherein an amount of the surface modifier (B) for the treatment ranges from 0.001 part by mass to 1 part by mass with respect to 100 parts by mass of the crosslinked polymer (A).

8. The absorbent article according to claim 6, wherein the surface modifier (B) is at least one member selected from the group consisting of an amino-modified polysiloxane, a carboxy-modified polysiloxane, and silica.

9. The absorbent article according to claim 1, wherein the absorbent body comprises an air-laid water absorption layer obtained by an air laying method; and a mass ratio of the water absorbent resin powder to a total mass of the air-laid water absorption layer ranges from 62.0 mass % to 99.5 mass %.

10. The absorbent article according to claim 1, wherein the absorbent body comprises a liquid permeable first sheet, a second sheet, and the water absorbent resin powder disposed between the first sheet and the second sheet; and a mass ratio of the water absorbent resin powder to a total mass of the absorbent body is 60 mass % or more.

11. The absorbent article according to claim 1, wherein the absorbent body is disposed on the upper surface side of the diffusion layer.

12. The absorbent article according to claim 1, wherein a planar view shape of the absorbent body is substantially identical to a planar view shape of the diffusion layer.

13. The absorbent article according to claim 1, wherein the water absorbent resin powder has a water retaining capacity ranging from 20 g/g to 30 g/g.

14. The absorbent article according to claim 1, wherein the material of the synthetic fiber constituting the synthetic fiber assembly is at least one selected from the group consisting of a polyolefin, a halogenated olefin, a polyester, a polyether, a polyacryl, a polyamide, a polystyrene, and a polycarbonate.

15. The absorbent article according to claim 1, wherein the synthetic fibers constituting the synthetic fiber assembly are not adhered and tangled intentionally.

16. The absorbent article according to claim 1, wherein the diffusion layer has a thickness ranging from 0.5 mm to 40 mm.

17. The absorbent article according to claim 1, wherein the diffusion layer has a mass ranging from 100 $g/m^2$ to 800 $g/m^2$ per unit area.

18. The absorbent article according to claim 1, wherein the synthetic fiber constituting the synthetic fiber assembly has a circular cross sectional shape or an elliptical cross sectional shape.

19. The absorbent article according to claim 1, wherein the synthetic fiber constituting the synthetic fiber assembly has a fineness ranging from 1 dtex to 60 dtex.

20. The absorbent article according to claim 1, wherein the absorbent article comprises one absorbent body and one diffusion layer, and the absorbent body is disposed on an upper surface side of the diffusion layer.

* * * * *